United States Patent [19]
Foley et al.

[11] Patent Number: 6,167,145
[45] Date of Patent: *Dec. 26, 2000

[54] BONE NAVIGATION SYSTEM

[75] Inventors: Kevin T. Foley, Germantown, Tenn.; Kurt R. Smith, Boulder, Colo.; John B. Clayton, Germantown, Tenn.

[73] Assignee: Surgical Navigation Technologies, Inc., Broomfield, Colo.

[ * ] Notice: This patent issued on a continued prosecution application filed under 37 CFR 1.53(d), and is subject to the twenty year patent term provisions of 35 U.S.C. 154(a)(2).

[21] Appl. No.: 08/623,956

[22] Filed: Mar. 29, 1996

[51] Int. Cl.$^7$ ...................................................... G06K 9/00
[52] U.S. Cl. ........................... 382/128; 600/426; 600/383
[58] Field of Search .................................... 382/294, 128; 364/413.15; 606/130, 383, 386, 407, 426, 414; 128/653.1

[56] References Cited

U.S. PATENT DOCUMENTS

| | | | |
|---|---|---|---|
| D. 291,246 | 8/1987 | Lower | D24/26 |
| D. 349,573 | 8/1994 | Bookwalter | D24/128 |
| D. 353,668 | 12/1994 | Banks | D24/112 |
| D. 357,534 | 4/1995 | Hayes | D24/140 |
| D. 359,557 | 6/1995 | Hayes | D24/140 |
| 3,821,469 | 6/1974 | Whetstone et al. | 178/18 |
| 3,868,565 | 2/1975 | Kuipers | 324/34 R |
| 3,910,258 | 10/1975 | Pisarski et al. | 128/2.1 B |
| 3,963,028 | 6/1976 | Cooley et al. | 128/276 |
| 3,971,133 | 7/1976 | Mushabac | 32/2 |

(List continued on next page.)

FOREIGN PATENT DOCUMENTS

| | | |
|---|---|---|
| 0 018 166 | 4/1980 | European Pat. Off. ........ A61B 19/00 |
| 0 062 941 | 10/1982 | European Pat. Off. .......... A61B 5/10 |
| 0 155 857 | 1/1985 | European Pat. Off. ......... G61O 7/00 |
| 0 207 452 | 1/1987 | European Pat. Off. ........ A61B 19/00 |
| 0 322 363 | 6/1989 | European Pat. Off. ........ A61B 17/14 |
| 0 326 768 | 8/1989 | European Pat. Off. ........ A61B 19/00 |
| 0 427 358 | 10/1990 | European Pat. Off. .......... A61B 6/00 |

(List continued on next page.)

*Primary Examiner*—Matthew C. Bella
*Attorney, Agent, or Firm*—Finnegan, Henderson, Farabow, Garrett & Dunner, L.L.P.

[57] ABSTRACT

A system for use during a medical or surgical procedure on a body. The system generates a display representing the position of two or more body elements during the procedure based on an image data set generated by a scanner prior to the procedure. The image data set has reference points for each of the body elements, the reference points of a particular body element having a fixed spatial relation to the particular body element. The system includes an apparatus for identifying, during the procedure, the relative position of each of the reference points of each of the body elements to be displayed. The system also includes a processor for modifying the image data set according to the identified relative position of each of the reference points during the procedure, as identified by the identifying apparatus, said processor generating a displaced image data set representing the position of the body elements during the procedure. The system also includes a display utilizing the displaced image data set generated by the processor, illustrating the relative position of the body elements during the procedure. Methods relating to the system are also disclosed.

20 Claims, 18 Drawing Sheets

U.S. PATENT DOCUMENTS

| | | | |
|---|---|---|---|
| 3,983,474 | 9/1976 | Kuipers | 324/43 B |
| 4,058,114 | 11/1977 | Soldner | 128/303 B |
| 4,068,156 | 1/1978 | Johnson et al. | 318/575 |
| 4,071,456 | 1/1978 | McGee et al. | 252/8.7 |
| 4,117,337 | 9/1978 | Staats | 250/445 |
| 4,182,312 | 1/1980 | Mushabac | 433/68 |
| 4,209,254 | 6/1980 | Reymond | 756/152 |
| 4,259,725 | 3/1981 | Andrews et al. | 364/521 |
| 4,262,306 | 4/1981 | Renner | 358/93 |
| 4,341,220 | 7/1982 | Perry | 128/630 |
| 4,358,856 | 11/1982 | Stivender et al. | 378/167 |
| 4,368,556 | 1/1983 | Wanner et al. | 16/111 R |
| 4,396,945 | 8/1983 | DiMatteo et al. | 358/107 |
| 4,398,540 | 8/1983 | Takemura et al. | 128/440 |
| 4,407,298 | 10/1983 | Lentz et al. | 128/713 |
| 4,419,012 | 12/1983 | Stephenson | 356/141 |
| 4,457,311 | 7/1984 | Sorenson et al. | 128/668 |
| 4,465,069 | 8/1984 | Barbier et al. | 128/303 B |
| 4,473,074 | 9/1984 | Vassiliadis | 128/303.1 |
| 4,506,676 | 3/1985 | Duska | 128/653 |
| 4,537,198 | 8/1985 | Crbett | 128/639 |
| 4,543,959 | 10/1985 | Sepponen | 128/653 |
| 4,571,834 | 2/1986 | Fraser et al. | 33/1 |
| 4,583,538 | 4/1986 | Onik et al. | 128/303 B |
| 4,585,350 | 4/1986 | Pryer et al. | 356/325 |
| 4,592,352 | 6/1986 | Patil | 128/303 B |
| 4,602,622 | 7/1986 | Bär et al. | 128/303 B |
| 4,608,977 | 9/1986 | Brown | 128/303 B |
| 4,638,798 | 1/1987 | Sheldon et al. | 128/303 B |
| 4,649,504 | 3/1987 | Krouglicof et al. | 364/559 |
| 4,651,732 | 3/1987 | Frederick | 128/303 R |
| 4,659,971 | 4/1987 | Suzuki et al. | 318/568 |
| 4,660,970 | 4/1987 | Ferrano | 356/1 |
| 4,672,306 | 6/1987 | Thong | 324/72.5 |
| 4,673,352 | 6/1987 | Hansen | 433/69 |
| 4,674,057 | 6/1987 | Caughman et al. | 364/513 |
| 4,686,997 | 8/1987 | Oloff et al. | 128/653 |
| 4,698,777 | 10/1987 | Toyoda et al. | 364/513 |
| 4,701,047 | 10/1987 | Eibert et al. | 356/1 |
| 4,701,049 | 10/1987 | Beckman | 356/1 |
| 4,705,395 | 11/1987 | Hageniers | 356/1 |
| 4,705,401 | 11/1987 | Addleman | 356/376 |
| 4,706,665 | 11/1987 | Gouda | 128/303 B |
| 4,709,156 | 11/1987 | Murphy | 250/560 |
| 4,721,384 | 1/1988 | Dietrich et al. | 356/1 |
| 4,721,388 | 1/1988 | Takagi et al. | 356/376 |
| 4,722,056 | 1/1988 | Roberts et al. | 364/413 |
| 4,723,544 | 2/1988 | Moore et al. | 128/303 B |
| 4,727,565 | 2/1988 | Ericson | 378/205 |
| 4,733,661 | 3/1988 | Palestrant | 128/303 B |
| 4,733,662 | 3/1988 | DeSatnick | 128/305 |
| 4,733,969 | 3/1988 | Case et al. | 356/375 |
| 4,737,032 | 4/1988 | Addleman et al. | 356/376 |
| 4,737,921 | 4/1988 | Goldwasser et al. | 364/518 |
| 4,742,815 | 5/1988 | Ninan et al. | 128/4 |
| 4,743,770 | 5/1988 | Lee | 250/560 |
| 4,743,771 | 5/1988 | Sacks et al. | 250/560 |
| 4,745,290 | 5/1988 | Frankel et al. | 250/560 |
| 4,750,487 | 6/1988 | Zanetti | 128/303 B |
| 4,753,128 | 6/1988 | Bartlett et al. | 74/469 |
| 4,753,528 | 6/1988 | Hines | 356/1 |
| 4,761,072 | 8/1988 | Pryor | 356/1 |
| 4,762,016 | 8/1988 | Stoughton et al. | 74/479 |
| 4,764,015 | 8/1988 | Bieringer et al. | 356/372 |
| 4,764,016 | 8/1988 | Johanasson | 356/371 |
| 4,767,934 | 8/1988 | Stauffer | 250/561 |
| 4,771,787 | 9/1988 | Wurster et al. | 128/660.03 |
| 4,775,235 | 10/1988 | Hecker et al. | 356/376 |
| 4,776,749 | 10/1988 | Wanzenberg et al. | 414/680 |
| 4,779,212 | 10/1988 | Levy | 364/562 |
| 4,782,239 | 11/1988 | Hirose et al. | 250/561 |
| 4,788,481 | 11/1988 | Niwa | 318/600 |
| 4,791,934 | 12/1988 | Brunnett | 128/653 |
| 4,793,355 | 12/1988 | Crum et al. | 128/653 |
| 4,794,262 | 12/1988 | Sato et al. | 250/560 |
| 4,803,645 | 2/1989 | Ohtomo et al. | 364/560 |
| 4,805,615 | 2/1989 | Carol | 128/303 B |
| 4,809,694 | 3/1989 | Ferrara | 128/303 B |
| 4,821,200 | 4/1989 | Oberg | 364/474.24 |
| 4,821,206 | 4/1989 | Arora | 364/513 |
| 4,822,163 | 4/1989 | Schmidt | 356/1 |
| 4,825,091 | 4/1989 | Breyer et al. | 250/560 |
| 4,829,373 | 5/1989 | Leberl et al. | 358/88 |
| 4,835,710 | 5/1989 | Schnelle et al. | 364/513 |
| 4,836,778 | 6/1989 | Baumrind et al. | 433/69 |
| 4,837,669 | 6/1989 | Tharp et al. | 362/418 |
| 4,841,967 | 6/1989 | Chang et al. | 128/303 B |
| 4,875,478 | 10/1989 | Chen | 128/303 B |
| 4,896,673 | 1/1990 | Rose et al. | 128/660.03 |
| 4,931,056 | 6/1990 | Ghajar et al. | 606/653 R |
| 4,933,843 | 6/1990 | Scheller et al. | 364/413.01 |
| 4,943,296 | 7/1990 | Funakubo et al. | 606/166 |
| 4,945,914 | 8/1990 | Allen | 128/653 R |
| 4,955,891 | 9/1990 | Carol | 606/130 |
| 4,961,422 | 10/1990 | Marchosky | 128/401 |
| 4,967,038 | 10/1990 | Gevins et al. | 128/644 |
| 4,982,188 | 1/1991 | Fodale et al. | 340/310.28 |
| 4,991,579 | 2/1991 | Allen | 128/653 R |
| 5,005,142 | 4/1991 | Lipchak et al. | 364/550 |
| 5,016,639 | 5/1991 | Allen | 128/653 R |
| 5,017,139 | 5/1991 | Mushabac | 433/109 |
| 5,027,818 | 7/1991 | Bova et al. | 128/653.1 |
| 5,039,867 | 8/1991 | Nishihara et al. | 250/492.3 |
| 5,047,036 | 9/1991 | Koutrouvelis | 606/130 |
| 5,050,608 | 9/1991 | Watanabe et al. | 128/653 R |
| 5,059,789 | 10/1991 | Salcudean et al. | 250/206.1 |
| 5,078,140 | 1/1992 | Kwoh | 128/653.1 |
| 5,078,142 | 1/1992 | Siczek et al. | 128/653.1 |
| 5,079,699 | 1/1992 | Tuy et al. | 364/413.22 |
| 5,080,662 | 1/1992 | Paul | 606/130 |
| 5,086,401 | 2/1992 | Glassman et al. | 395/94 |
| 5,094,241 | 3/1992 | Allen | 128/653.1 |
| 5,097,839 | 3/1992 | Allen | 128/653.1 |
| 5,099,846 | 3/1992 | Hardy | 606/130 X |
| 5,107,839 | 4/1992 | Houdek et al. | 606/130 X |
| 5,119,817 | 6/1992 | Allen | 128/653.1 |
| 5,142,930 | 9/1992 | Allen et al. | 74/469 |
| 5,178,164 | 1/1993 | Allen | 128/898 |
| 5,186,174 | 2/1993 | Schlöndorff et al. | 128/653.1 |
| 5,193,106 | 3/1993 | DeSana | 378/163 |
| 5,197,476 | 3/1993 | Nowacki et al. | 128/660 |
| 5,198,877 | 3/1993 | Schulz | 356/375 |
| 5,207,223 | 5/1993 | Adler | 128/653.1 |
| 5,211,164 | 5/1993 | Allen | 128/653.1 |
| 5,222,499 | 6/1993 | Allen et al. | 128/653.1 |
| 5,224,049 | 6/1993 | Mushabac | 364/474.05 |
| 5,230,338 | 7/1993 | Allen et al. | 128/653 |
| 5,249,581 | 10/1993 | Horbal et al. | 128/664 |
| 5,251,127 | 10/1993 | Raab | 364/413 |
| 5,257,998 | 11/1993 | Ota et al. | 606/130 |
| 5,261,404 | 11/1993 | Mick et al. | 128/653.1 |
| 5,279,309 | 1/1994 | Taylor et al. | 128/782 |
| 5,291,889 | 3/1994 | Kenet et al. | 128/653.1 |
| 5,295,200 | 3/1994 | Boyer | 382/43 |
| 5,295,483 | 3/1994 | Nowacki et al. | 128/660.03 |
| 5,299,288 | 3/1994 | Glassman et al. | 395/80 |
| 5,305,091 | 4/1994 | Gelbart et al. | 356/375 |
| 5,305,203 | 4/1994 | Raab | 364/413 |
| 5,309,913 | 5/1994 | Kormos et al. | 128/653.1 |
| 5,313,944 | 5/1994 | Crowley et al. | 128/693.1 |
| 5,355,129 | 10/1994 | Baumann | 340/870.04 |
| 5,357,953 | 10/1994 | Merrick et al. | 128/633 |

| | | | |
|---|---|---|---|
| 5,359,417 | 10/1994 | Müller et al. | 356/375 |
| 5,368,030 | 11/1994 | Zinreich et al. | 128/653.1 |
| 5,371,778 | 12/1994 | Yanof et al. | 364/413.22 |
| 5,383,454 | 1/1995 | Bucholz . | |
| 5,389,101 | 2/1995 | Heilbrum et al. | 606/130 |
| 5,391,199 | 2/1995 | Ben-Haim | 607/122 |
| 5,398,684 | 3/1995 | Hardy | 128/653.1 |
| 5,399,146 | 3/1995 | Nowacki et al. | 601/4 |
| 5,399,951 | 3/1995 | Lavalee et al. | 318/567 |
| 5,443,489 | 8/1995 | Ben-Haim | 607/115 |
| 5,447,154 | 9/1995 | Cinquin et al. | 128/653.1 |
| 5,480,422 | 1/1996 | Ben-Haim | 607/122 |
| 5,483,961 | 1/1996 | Kelly et al. | 128/653.1 |
| 5,490,196 | 2/1996 | Rudich et al. | 378/101 |
| 5,494,034 | 2/1996 | Schlöndorff et al. . | |
| 5,515,160 | 5/1996 | Schulz et al. | 356/241 |
| 5,517,990 | 5/1996 | Kalfas et al. | 128/653.1 |
| 5,526,576 | 6/1996 | Fuchs et al. | 33/503 |
| 5,531,227 | 7/1996 | Schneider | 128/653.1 |
| 5,531,520 | 7/1996 | Grimson et al. | 382/131 |
| 5,546,951 | 8/1996 | Ben-Haim | 128/702 |
| 5,551,429 | 9/1996 | Fitzpatrick et al. | 128/653.1 |
| 5,558,091 | 9/1996 | Acker et al. | 128/653.1 |
| 5,568,809 | 10/1996 | Ben-Haim | 128/656 |
| 5,603,318 | 2/1997 | Heilbrum et al. | 128/630 |
| 5,617,857 | 4/1997 | Chader et al. | 128/653.1 |
| 5,622,170 | 4/1997 | Schulz | 128/653.1 |
| 5,638,819 | 6/1997 | Manwaring et al. | 128/653.1 |
| 5,647,361 | 7/1997 | Damadian | 128/683.1 |
| 5,662,111 | 9/1997 | Cosman | 128/653.1 |
| 5,682,886 | 11/1997 | Delp et al. | 128/653.1 |
| B1 5,383,454 | 12/1996 | Bucholz | 128/653.1 |

FOREIGN PATENT DOCUMENTS

| | | | |
|---|---|---|---|
| 0 469 966 A1 | 7/1991 | European Pat. Off. | A61B 19/00 |
| 0 456 103 | 11/1991 | European Pat. Off. | A61B 19/00 |
| 0 581 704 A1 | 7/1993 | European Pat. Off. | A61B 8/14 |
| 0 359 773 | 10/1993 | European Pat. Off. | A61B 19/00 |
| 0 603 089 A1 | 12/1993 | European Pat. Off. | A61B 19/00 |
| 0 501 993 | 5/1996 | European Pat. Off. | G06T 17/00 |
| 2 417 970 | 10/1979 | France | 128/653.1 |
| 2534516A1 | 2/1976 | Germany | G03B 17/26 |
| 2852949A | 6/1980 | Germany | G03B 17/26 |
| 3205085A1 | 9/1982 | Germany | A61B 19/00 |
| 3205915A1 | 9/1983 | Germany | A61B 17/34 |
| 3508730A1 | 9/1986 | Germany | A61B 5/10 |
| 87 01 668 | 2/1987 | Germany | A61B 17/36 |
| 3 205 915 | 9/1993 | Germany | A61B 17/34 |
| 4432890A1 | 3/1996 | Germany | A61N 5/10 |
| 62-000327 | 1/1987 | Japan | A61B 6/03 |
| 2 094 590 | 9/1982 | United Kingdom | 128/653.1 |
| WO 88/09151 | 12/1988 | WIPO | A61B 19/00 |
| WO 90/05494 | 5/1990 | WIPO | A61B 19/00 |
| WO 91/04711 | 4/1991 | WIPO | A61B 19/00 |
| WO 91/07726 | 5/1991 | WIPO | G06F 15/72 |
| WO 92/06645 | 4/1992 | WIPO | A61B 19/00 |
| WO 92/00702 | 12/1992 | WIPO | A61B 19/00 |
| WO 93/10710 | 6/1993 | WIPO | A61B 6/00 |
| WO 93/2052 | 10/1993 | WIPO | C07D 211/48 |
| WO 93/20528 | 10/1993 | WIPO | G06F 15/72 |
| WO 94/06352 | 3/1994 | WIPO | A61B 6/04 |
| WO 94/23647 | 10/1994 | WIPO | A61B 5/05 |
| WO 94/24933 | 10/1994 | WIPO | A61B 5/05 |
| WO 94/24933 | 11/1994 | WIPO | A61B 5/05 |
| WO9424933 | 11/1994 | WIPO | A61B 5/05 |
| WO 95/11624 | 5/1995 | WIPO | A61B 5/00 |
| WO 96/1624 | 4/1996 | WIPO | A61B 5/00 |

ALIGNMENT DURING SCANNING

ALIGNMENT DURING SURGERY

BONE NAVIGATION SYSTEM

BACKGROUND OF THE INVENTION

The invention relates generally to systems which generate images during medical and surgical procedures, and in particular, a system for generating images during medical and surgical procedures based on a scan taken prior to the procedure.

Image guided medical and surgical procedures comprise a technology by which images, obtained either preprocedurally or intraprocedurally (i.e., prior to or during a medical or surgical procedure), are used to guide a doctor during the procedure. The recent increase in interest in this field is a direct result of the recent advances in imaging technology, especially in devices using computers to generate three dimensional images of parts of the body, such as computed tomography (CT) or magnetic resonance imaging (MRI).

The majority of the advances in imaging involve devices which tend to be large, encircle the body part being imaged, and are expensive. Although the images produced by these devices depict the body part under investigation with high resolution and good spatial fidelity, their cost usually precludes the dedication of a unit to the performance of procedures. Therefore, image guided surgery is usually performed using images taken preoperatively.

The reliance upon preoperative images has focused image guidance largely to the cranium. The skull, by encasing the brain, serves as a vessel which inhibits changes in anatomy between imaging and surgery. The skull also provides a relatively easy point of reference to which a localization system may be attached so that registration of preprocedural images to the procedural work space can be done simply at the beginning of the procedure. Registration is defined as the process of relating preprocedural images of anatomy to the surgical or medical position of the corresponding anatomy. For example, see Ser. No. 07/909,097, now U.S. Pat. No. 5,383,454, and PCT application PCT/US95/12894 filed on Oct. 5, 1995, entitled "Surgical Navigation Systems Including Reference and Localization Frames," the entire disclosures of which are incorporated herein by reference.

This situation of rigid fixation and absence of anatomical movement between imaging and surgery is unique to the skull and intracranial contents and permits a one-to-one registration process as shown in FIG. 1. The position during a medical procedure or surgery is in registration with the preprocedural image data set because of the absence of anatomical movement from the time of the scan until the time of the procedure. In almost every other part of the body there is ample opportunity for movement which degrades the fidelity of the pre-procedural images in depicting the intra-procedural anatomy. Therefore, additional innovations are needed to bring image guidance to the rest of the body beyond the cranium.

The accuracy of image guided surgery is based on the identification of structures within the body that do not change shape, do not compress, nor deform between the process of imaging and surgery. Such structures are termed "rigid bodies," and the bones of the skeleton satisfy this definition for a rigid body. Bones are commonly a target for medical or surgical procedures either for repair, fusion, or biopsy. Therefore, a technique is needed whereby registration can be performed between the bones or bone fragments (skeletal elements) as depicted pre-procedurally on scans and the position of these same skeletal elements as detected intraprocedurally. This technique must take into account that movement can occur between portions of the skeleton which are not rigidly joined, such as bones connected by a joint, or fragments of a broken bone.

SUMMARY OF THE INVENTION

It is an object of this invention to provide a system which allows registration between multiple skeletal elements depicted in pre-procedural images and detected during surgery.

It is a further object of this invention to provide a system which can localize multiple rigid bodies that move with respect to each other between imaging and a procedure and provide a display during the procedure of the bodies in their displaced positions.

It is another object of this invention to provide a system for use during a medical or surgical procedure on the body, the system generating a display representing the position of two or more body elements during the procedure based on an image data set generated by a scanner prior to the procedure.

It is another object of this invention to provide a system for use during a medical or surgical procedure on a body which modifies the image data set according to the identified relative position of each of the elements during the procedure.

It is another object of this invention to provide a system which generates a display representative of the position of a medical or surgical instrument during a procedure in relation to body elements.

It is a further object of this invention to provide a system for use during image guided medical and surgical procedures which is easily employed by the doctor or surgeon conducting the procedure.

It is another object of this invention to provide a system which determines the relative position of body elements based on the contour of the body elements which, in some cases, avoids the need for exposing the body elements.

It is still another object of this invention to provide a system which employs the projected fluoroscopic images of body elements to determine their relative position.

It is yet a further object of this invention to describe a surgical or medical procedure which employs a display representing the position of body elements during the procedure based on an image data set of the body elements generated prior to the procedure.

It is a further object of this invention to provide a system and method for medical or surgical procedures which allows repositioning of body elements during the procedure and still permits the generation of a display showing the relative position of the body elements.

Other objects and features will be in part apparent and in part pointed out hereinafter.

The invention comprises system for use during a medical or surgical procedure on a body. The system generates a display representing the position of two or more body elements during the procedure based on an image data set generated by a scanner prior to the procedure, the image data set having reference points for each of the body elements. The reference points of a particular body element have a fixed spatial relation to the particular body element. The system includes means for identifying, during the procedure, the relative position of each of the reference points of each of the body elements to be displayed. The system also includes a processor modifying the image data set according to the identified relative position of each of the reference points during the procedure, as identified by the identifying means. The processor generates a displaced image data set representing the position of the body elements during the procedure. The system also includes a display utilizing the displaced image data set generated by the processor and illustrating the relative position of the body elements during the procedure.

The invention also comprises a method for use during a procedure. The method generates a display representing the position of two or more body elements during the procedure based on an image data set generated prior to the procedure, which image data set has reference points for each of the body elements. The method comprises the steps of:

identifying, during the procedure, the relative position of each of the reference points of each of the body elements to be displayed;

modifying the image data set according to the identified relative position of each of the reference points during the procedure in order to generate a displaced image data set representing the position of the body elements during the procedure; and generating a display based on the displaced image data set illustrating the relative position of the body elements during the procedure.

The invention also comprises a method for use with two or more body elements which each have reference points. The method comprises the steps of:
prior to a procedure:
placing the body elements in a frame to fix their relative position; and
scanning the fixed body elements; and during the procedure:
placing the body elements in the frame so that the body elements have the same relative position as their position during scanning;
determining the position of reference points on the body elements relative to reference means;
determining the position of a medical or surgical instrument relative to the reference means;
determining the position of the medical or surgical instrument relative to the body elements; and
generating a display based on the preprocedural scanning illustrating the determined position of the medical or surgical instrument relative to the body elements.

BRIEF DESCRIPTION OF THE DRAWINGS

Corresponding reference characters indicate corresponding parts throughout the drawings.

DETAILED DESCRIPTION OF THE PREFERRED EMBODIMENTS

Figure 1:
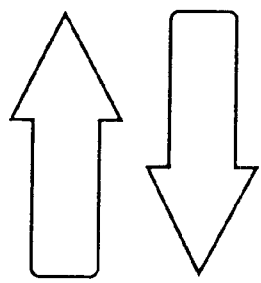
FIG. 1 is an illustration of the prior art system in which rigid fixation and absence of movement between imaging and surgery permits a one-to-one registration process between the pre-surgical image data set and the position in surgery.
Figure 1:
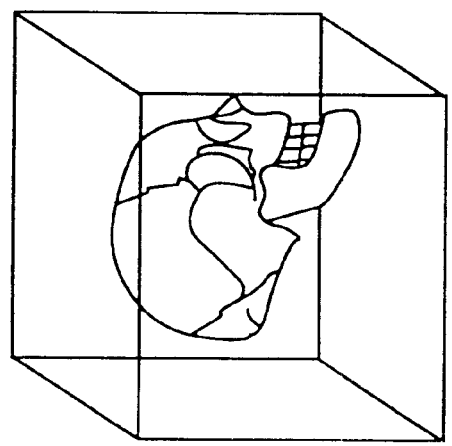
Figure 2A:
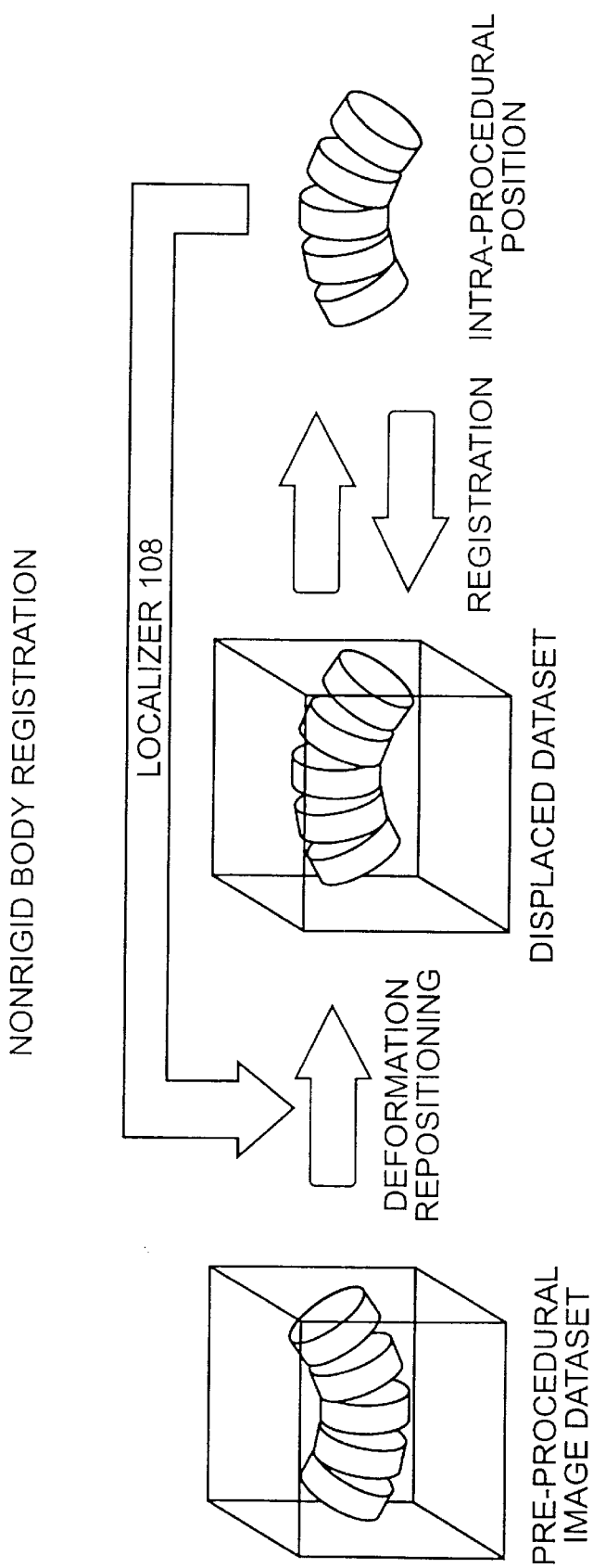
FIG. 2A is an illustration of operation of the invention in which the preprocedural image data set is modified in accordance with the intraprocedural position in order to generate a displaced data set representative of the intraprocedural position.
Figure 2B:
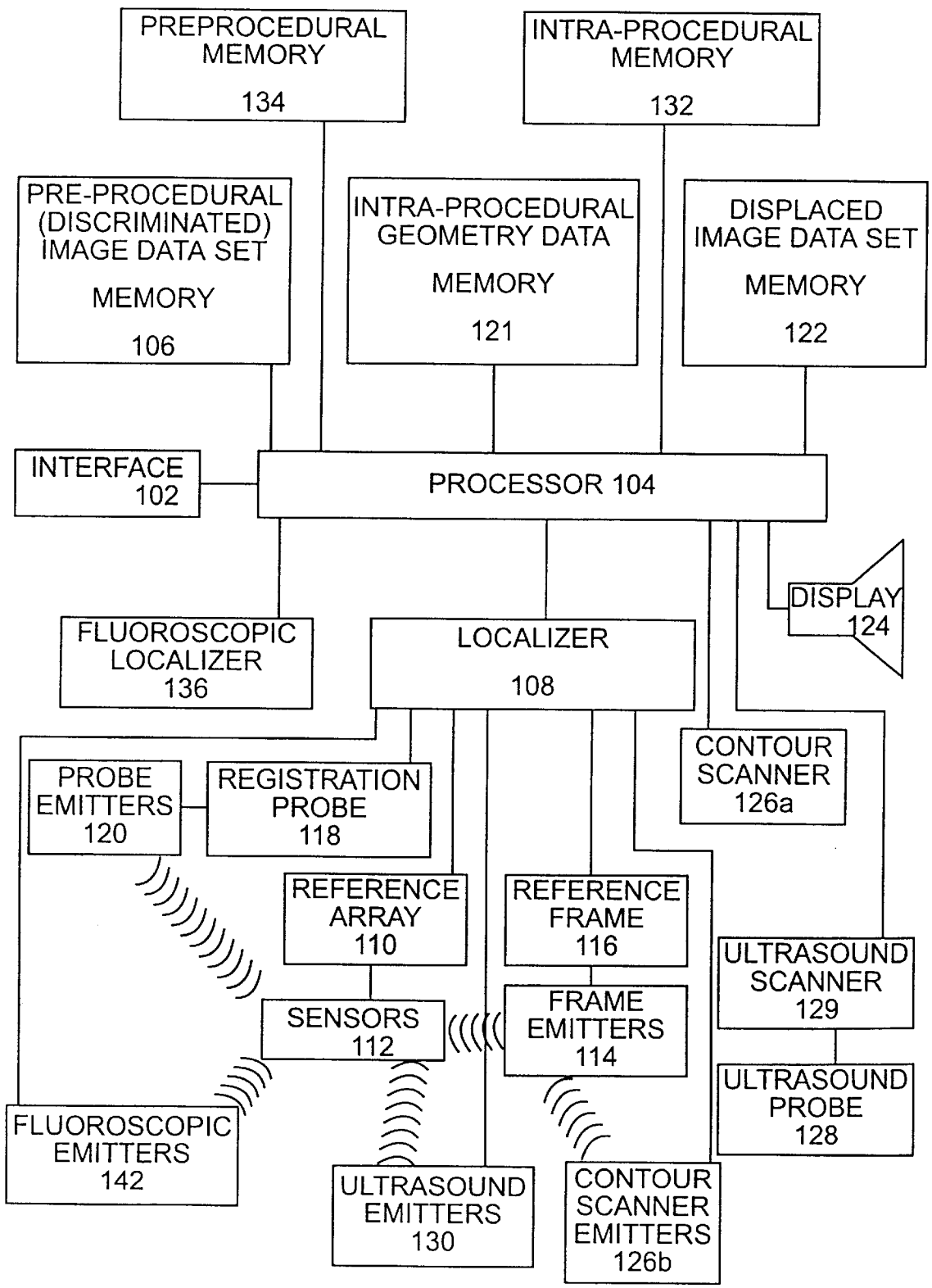
FIG. 2B is a block diagram of one preferred embodiment of a system according to the invention.
Figure 3:
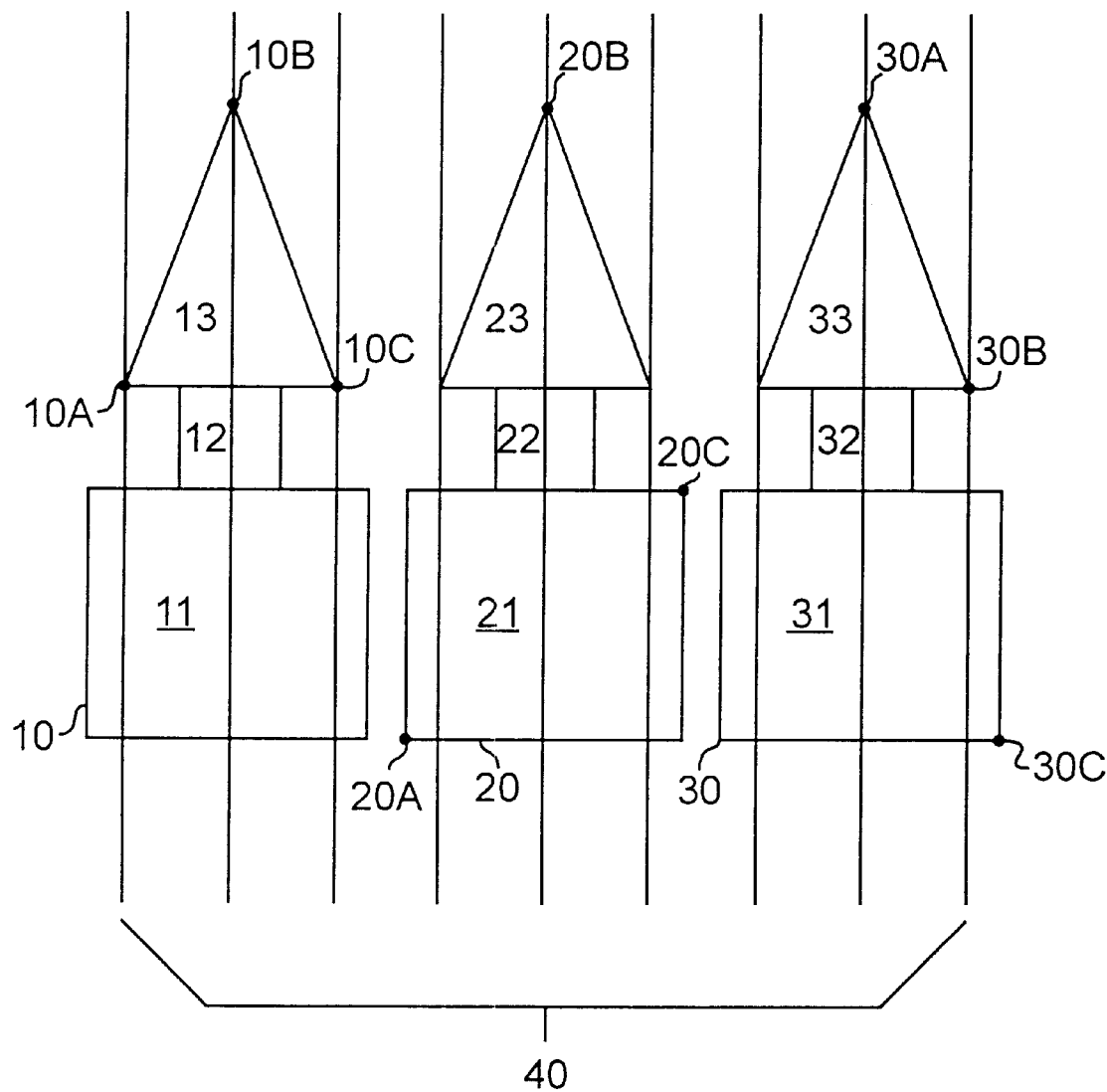
FIG. 3 is an illustration of the preprocedural alignment of three body elements during scanning.

Referring to FIGS. 2A and 2B, an overview of operation of one preferred embodiment of the system according to the invention is illustrated. Prior to a particular procedure, the body elements which will be part of the procedure are scanned to determine their alignment. For example, the alignment may be such as illustrated in FIG. 3 wherein body elements 10, 20, and 30 are more or less aligned in parallel. These body elements may be bones or other rigid bodies. In FIG. 3, three-dimensional skeletal elements 10, 20, 30 are depicted in two dimensions as highly stylized vertebral bodies, with square vertebra 11, 21, 31, small rectangular pedicles 12, 22, 32, and triangular spinous processes 13, 23, 33. During imaging, scans are taken at intervals through the body parts 10, 20, 30 as represented in FIG. 3 by nine straight lines generally referred to by reference character 40. At least one scan must be obtained through each of the body elements and the scans taken together constitute a three-dimensional preprocedural image data set.

FIG. 2B is a block diagram of the system according to the invention. A scanner interface 102 allows a processor 104 to obtain the preprocedural image data set generated by the scanner and store the data set in preprocedural image data set memory 106. Preferably, after imaging, processor 104 applies a discrimination process to the pre-procedural image data set so that only the body elements 10, 20, 30 remain in memory 106. If a discrimination process is employed, processor 104 may execute the discrimination process while data is being transferred from the scanner through the scanner interface 102 for storage in memory 106. Alternatively, memory 106 may be used for storing undiscriminated data and a separate memory (not shown) may be provided for storing the discriminated data. In this alternative, processor 104 would transfer the data set from the scanner through scanner interface 102 into memory 106 and then would discriminate the data stored in memory 106 to generate a discriminated image data set which would be stored in the separate memory.

Once the body elements 10, 20, 30 are discriminated from the soft tissue and each defined as a single rigid body, they can be repositioned by software algorithms, well known in the art, to form the displaced image data set. Each of the body elements 10, 20, 30 must have at least three reference points which are selected by the doctor or surgeon and which are visible on the preprocedural images. These reference points must be able to be indicated with accuracy during the procedure. For body part 10, reference points 10A, 10B, and 10C are located on the spinous process 13; for body part 20, reference points 20A and 20C are located on the vertebra 21 and reference point 20B is located on spinous process 23; and for body part 30, reference points 30A and 30B are located on the spinous process 33 and reference point 30C is located on the vertebra 31. More than one reference point can be selected on each scan through the bone, although the maximal accuracy of registration is achieved by separating the reference points as far as possible. For example, in the case of posterior spinal surgery, it may be preferable to select reference points 10A, 10B, and 10C on the spinous process which is routinely exposed during such surgery. It is contemplated that work station software may allow the manual or automated identification of these same points on the images of the body elements 10, 20, 30. As FIG. 3 is a two-dimensional simplification of a three-dimensional process, the reference points will not necessarily be limited to a perfect sagittal plane, as depicted.

After imaging, the skeletal body elements 10, 20, 30 may move with respect to each other at the joints or fracture lines. In the procedure room, such as an operating room or a room where a medical procedure will be performed, after positioning the patient for the surgery, the body elements will assume a different geometry, such as the geometry depicted in FIG. 4.

Figure 4:
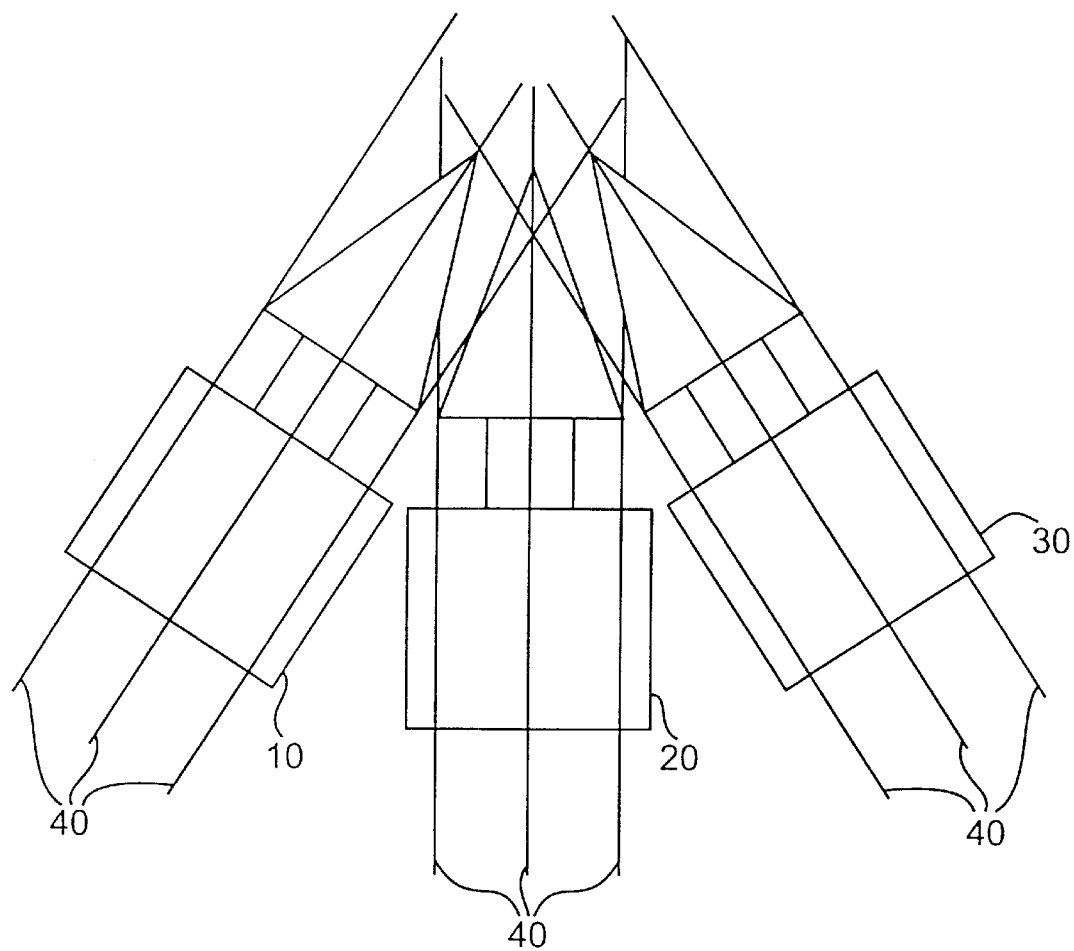
FIG. 4 is an illustration of the intraprocedural alignment of the three body elements of FIG. 3 during surgery.
Figure 5:
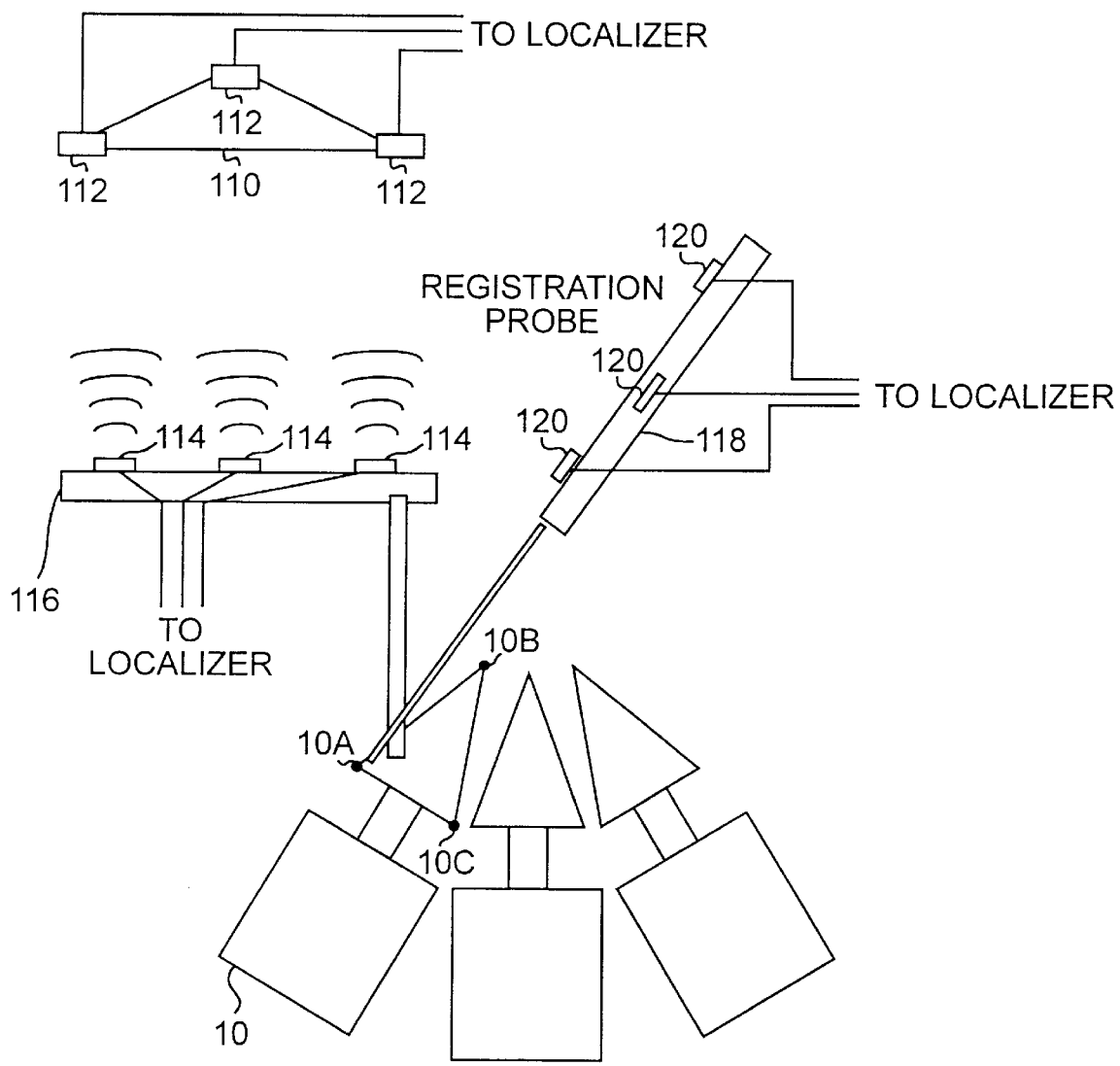
FIG. 5 is an illustration of three body elements, one of which has a reference frame attached thereto, in combination with a registration probe.

As a result of this movement, the preprocedural image data set stored in memory 106, consisting of the scans through the skeletal elements, does not depict the operative position of the skeletal elements, as shown in FIG. 4. However, the shape of the skeletal elements, as depicted by the scans through the element, is consistent between imaging and procedure, as indicated by the lines 40 through each element in FIG. 4. Therefore, the image data set must be modified to depict the current geometry of the skeletal elements. This modification is performed by identifying the location of each reference point of each skeletal element in procedure space. As diagrammatically illustrated in FIG. 2, a localizer 108 identifies the location and provides this information so that the preprocedural data set may be deformed or repositioned into the displaced data set. As a result, the displaced data set is in registration with the intraprocedural position of the elements 10, 20, 30. Once the locations of the reference points are determined by the localizer 108, processor 104, which is a part of the work station, can execute software which repositions the images of the skeletal elements to reflect the position of the actual elements in the procedure room thus forming the displaced set and the registration between the displaced set and the intraprocedural position.

Preferably, a three-dimensional digitizer may be used as the localizer 108 to determine the position and space of the elements 10, 20, 30 during the procedure. In general, the digitizer would include a reference array 110 which receives emissions from a series of emitters. Usually, the emissions consist of some sort of energy, such as light, sound or electromagnetic radiation. The emitters are applied to and positioned in coordination with the elements being localized and the reference array 110 is distant therefrom, determining the position of the emitters. As is apparent, the emitters may be placed distant to the elements and the reference array 110 may be attached to the elements being localized.

According to one preferred embodiment of the invention, a reference frame 116 is attached to one of the skeletal elements 10 at the beginning of the procedure. Reference array 110 is equipped with a plurality of emitters 114 which together define a three-dimensional procedural coordinate system with respect to the skeletal element 10. Emitters 114 communicate with sensors 112 on a reference array 110 located in the procedure room and remote from the reference frame 116 and patient. If the body of the patient is not immobilized during surgery, then multiple reference frames may be required. The three-dimensional procedural coordinate system may alternatively be defined by rigid fixation of the frame emitters 114 directly (or indirectly, for example, to the skin) to the skeletal elements 10, 20, or 30. In either case, the emitters 114 emit a signal which is received by the sensors 112. The received signal is digitized to compute position, for example, by triangulation. Through such information, the localizer 108 or a digitizer which is part of the localizer 108 can determine the exact three-dimensional position of the frame emitters 114 relative to the sensors 112. Since the sensors 112 are in a fixed position throughout the procedure, as the reference array 110 is fixed in the procedure room to the ceiling or other support. Thereby, localizer 108 or the processor 104 can exactly determine the position of the reference frame 116 relative to the array which is free to move except during localization, e.g., activation of the emitters 114 on the reference frame 116 and activation of the probe emitters 120. Emitters 114 of the reference frame 116 are energized to provide radiation to the sensors 112, which radiation is received and generates signals provided to the localizer 108 for determining the position of the frame 116 relative to the array 110.

Next, it is necessary to determine the position of the skeletal element 10 to which the reference frame 116 is affixed. In particular, the position of the skeletal element 10 relative to the reference frame 116 must be determined. After exposure of the reference points 10A, 10B, 10C by surgical dissection, the reference points are touched by the tip of a registration probe 118 equipped with emitters 120. As each of the reference points 10A, 10B, 10C is touched by the tip of the probe 118, the emitters are energized to communicate with the sensors 112 of reference array 110. This communication permits the localizer 108 to determine the position of the registration probe 118, thereby determining the position of the tip of the probe 120, thereby determining the position of the reference point 10A on which the tip is positioned. By touching each of the reference points 10A, 10B, 10C on each skeletal element 10, 20, 30 involved in the procedure, and relating them to their corresponding reference points on the images of the same elements, an intraprocedural position data is generated and stored in memory 121. This data is used to derive a transformation which allows the determination of the exact procedural position and orientation of each skeletal element. Using the intraprocedural position of the skeletal elements 10, 20, 30, localizer 108 and processor 104 employ software which manipulates the preprocedural image data set stored in memory 106 to produce a displaced image data set which is stored in memory 122. The displaced image data set in memory 122 reflects the geometry of the actual elements 10, 20, 30 during the procedure. Processor 104 displays the displaced image data set on display 124 to provide a visual depiction of the relative position of the skeletal elements 10, 20, 30 during the procedure. This image is used by the doctor during the procedure to assist in the procedure. In addition, it is contemplated that an instrument which would be used during the procedure may be modified by the addition of emitters. This modified instrument when moved into the area of the skeletal elements 10, 20, 30 would be activated so that its emitters would communicate with the reference array 110 thereby permitting localizer 108 to determine the instrument's position. As a result, processor 104 would modify display 124 to indicate the position of the instrument, such as by positioning a cursor.

Reference frame 116 allows the patient to be moved during the procedure without the need for reregistering the position of each of the body elements 10, 20, 30. It is assumed that during the procedure, the patient is immobilized so that the body elements are fixed relative to each other. Since the reference frame 116 is affixed to skeletal element 10, movement of the patient results in corresponding movement of the reference frame 116. Periodically, or after each movement of the patient, array emitters 114 may be energized to communicate with the sensors 112 of reference array 110 in order to permit localizer 108 to determine the position of the reference frame 116. Since the reference frame 116 is in a fixed relative position to element 110 and since we have assumed that elements 20 and 30 are in fixed relation to element 10, localizer 108 and/or processor 104 can determine the position of the elements. From this position, a displaced image data set memory can be created for display on display 124.

An alternative to touching the reference points A, B, C with the tip of the probe 118 would be to use a contour scanner 126a and contour scanner emitters 126b. Such a device, using some form of energy such as sound or light which is emitted, reflected by the contour and sensed, would allow the extraction of a contour of the skeletal elements 10, 20, 30, thus serving as a multitude of reference points which would allow registration to occur. The registration process is analogous to the process described for ultrasound extracted contours below.

In certain situations, markers may be used on the skin surface as reference points to allow the transformation of the pre-procedural image data set into the displaced image data set. Reciprocally, skin surface fiducials applied at the time of imaging can be used to re-position the body to match the geometry during imaging and is described below.

Localization of skeletal elements 10, 20, 30 may be desired without intraprocedural exposure of the reference points A, B, C on those skeletal elements. Examples wherein the spine is minimally exposed include percutaneous biopsy of the spine or discectomy, spinal fixation, endoscopy, percutaneous spinal implant insertion, percutaneous fusion, and insertion of drug delivery systems. In this situation, localization of reference points on the skeletal elements must be determined by some form of imaging which can localize through overlying soft tissue. There are currently two imaging techniques which are available to a surgeon in the operating room or a doctor in a procedure room which satisfy the needs of being low cost and portable. Both imaging techniques, ultrasonography and radiography, can produce two- or three-dimensional images which can be employed in the fashion described herein to register a three-dimensional form such as a skeletal element.

Figure 6:
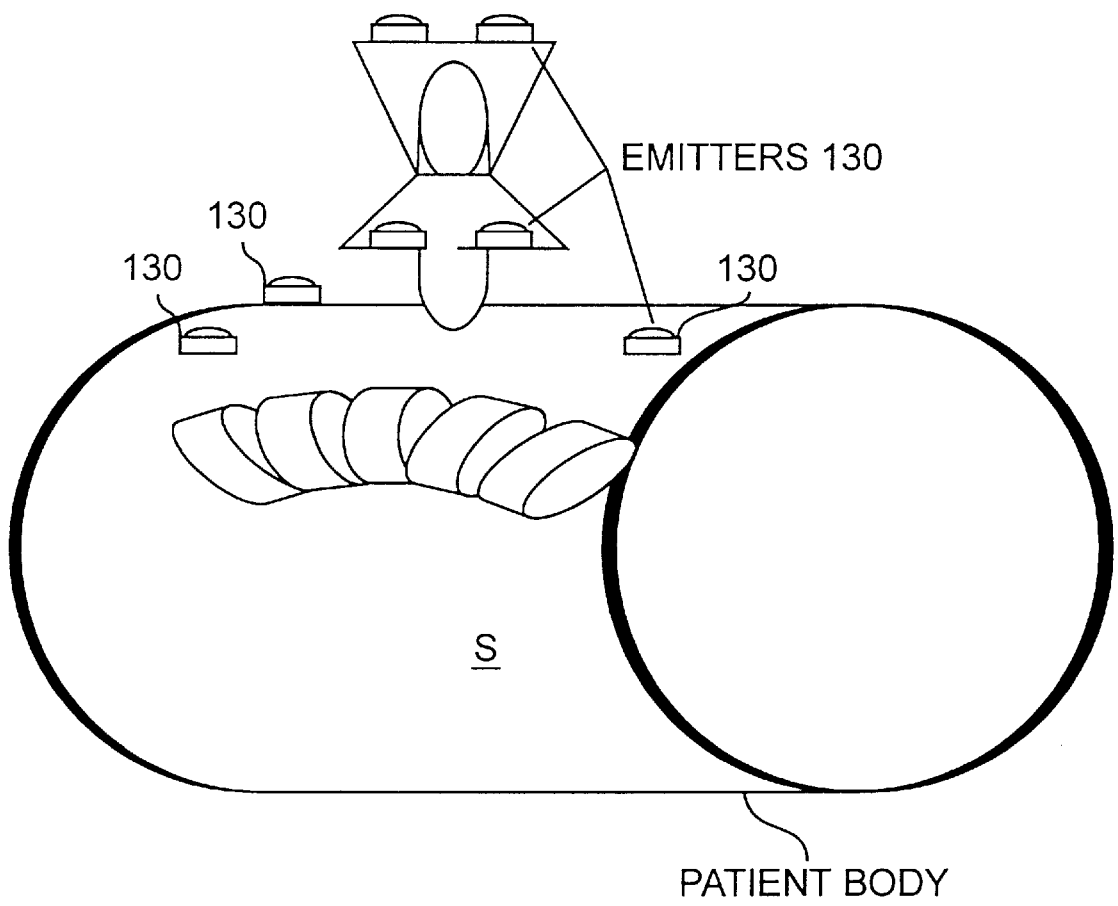
FIG. 6 is an illustration showing ultrasound registration according to the invention in which emitters are attached to the patient's body.

As described in U.S. patent application Ser. Nos. 07/858, 980 and 08/053,076, the entire disclosures of which are incorporated herein by reference, the coupling of a three-dimensional digitizer to a probe of an ultrasound device affords benefits in that a contour can be obtained which can be related directly to a reference system that defines three-dimensional coordinates in the procedural work space. In the context of the present invention, a patient is imaged prior to a procedure to generate a preprocedural image data set which is stored in memory 106. In the procedure room, the patient's body is immobilized to stabilize the spatial relationship between the skeletal elements 10, 20, 30. A reference system for the body is established by attaching a reference array 110 to one of the skeletal elements or by otherwise attaching emitters to the patient or skeletal elements as noted above. For example, this could be performed by using the percutaneous placement of a reference system similar to the one described above, radiopaque markers screwed into the elements or by placing emitters 130 directly, on the skin, as illustrated in FIG. 6, based on the assumption that the skin does not move appreciably during the procedure or in respect to the axial skeleton.

An ultrasound probe 128 equipped with at least three emitters 130 is then placed over the skeletal element of interest. The contour (which can be either two- or three-dimensional) of the underlying bone/soft tissue interface is then obtained using the ultrasound probe 128. This contour of the underlying bone can be expressed directly or indirectly in the procedural coordinates defined by the reference system. Emitters 130 communicate with sensors 112 of reference array 110 to indicate the position of the ultrasound probe 128. An ultrasound scanner 129 which energizes probe 128 determines the contour of the skeletal element of interest and being scanned. This contour information is provided to processor 104 for storage in contour memory 132.

The intraprocedural contour stored in memory 132 is then compared by a contour matching algorithm to a corresponding contour extracted from the preoperative image data set stored in memory 106. Alternatively, a preprocedural contour data set may be stored in memory 134 based on a preprocedural ultrasound scan which is input into memory 134 via scanner interface 102 prior to the procedure. This comparison process continues until a match is found for each one of the elements. Through this contour matching process, a registration is obtained between the images of each skeletal element and the corresponding position of each element in the procedural space.

In certain instances, the ultrasound registration noted above may not be applicable. For example, ultrasound does not penetrate bone, and the presence of overlying bone would preclude the registration of an underlying skeletal element. Further, the resolution of ultrasound declines as the depth of the tissue being imaged increases and may not be useful when the skeletal element is so deep as to preclude obtaining an accurate ultrasonically generated contour. In these circumstances, a radiological method is indicated, which utilizes the greater penetrating power of x rays.

Figure 7:
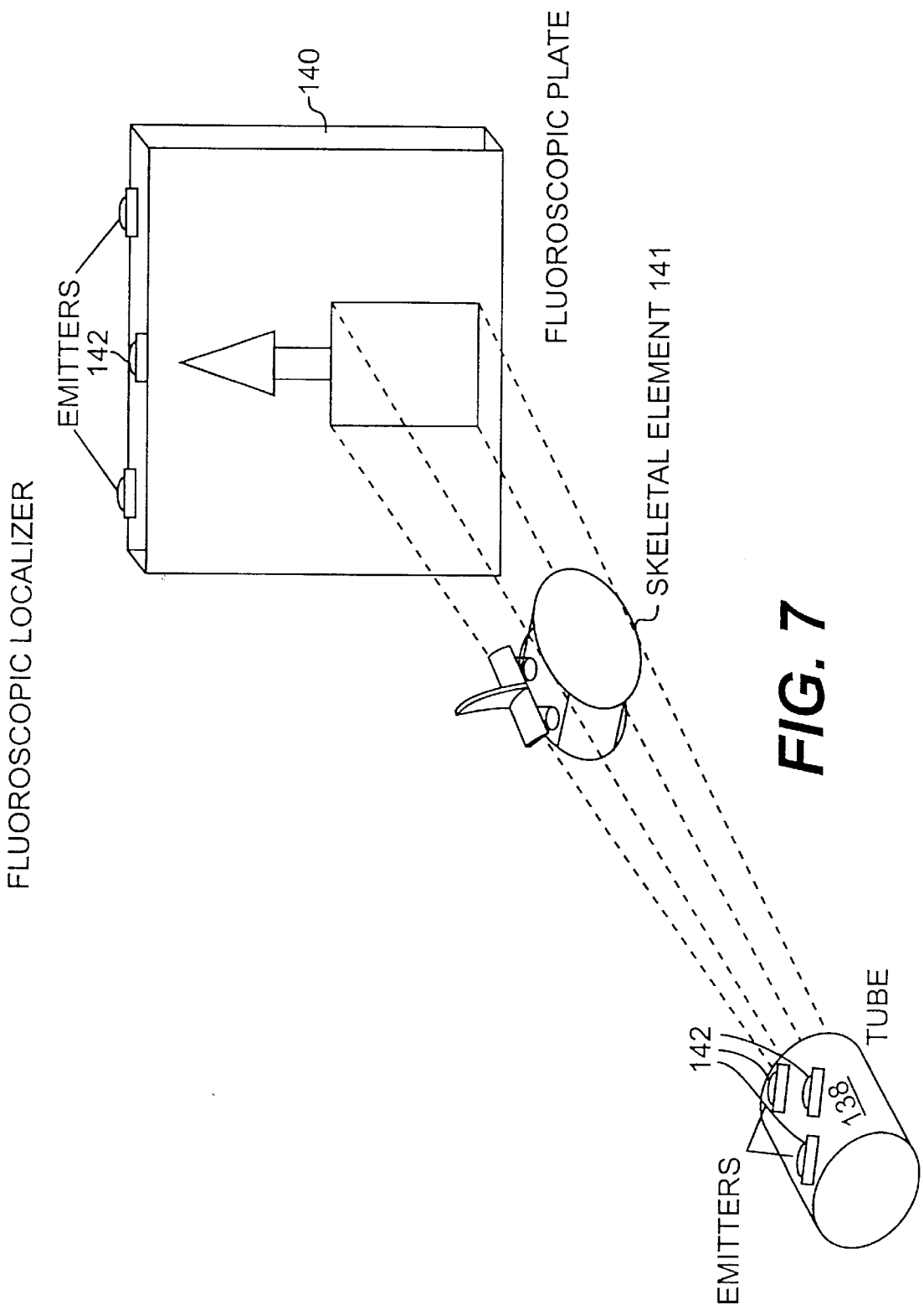
FIG. 7 is an illustration of a fluoroscopic localizer according to the invention for providing projections of an image of the body elements.

Preoperative imaging occurs as usual and the skeletal elements are discriminated from the soft tissue in the image data set as above. In particular, a CT scan of the skeletal elements 10, 20, 30 is taken prior to the procedure. Processor 104 may then discriminate the skeletal elements. Next, the patient is immobilized for the procedure. A radiograph of the skeletal anatomy of interest is taken by a radiographic device equipped with emitters detectible by the digitizer. For example, a fluoroscopic localizer 136 is illustrated in FIG. 7.

Localizer 136 includes a device which emits x rays such as tube 138 and a screen 140 which is sensitive to x rays, producing an image when x rays pass through it. In general, this screen is referred to as a fluoroscopic plate. Emitters 142 may be positioned on the tube 138, or on the fluoroscopic plate 140 or on both. For devices in which the tube 138 is rigidly supported relative to the plate 140, emitters need only be provided on either the tube or the plate. Alternatively, the reference array 110 may be attached to the tube or the plate. By passing x rays through the skeletal element 141 of interest, a two-dimensional image based on bone density is produced and recorded by the plate. The image produced by the fluoroscopic localizer 136 is determined by the angle of the tube 138 with respect to the plate 140 and the position of the skeletal elements therebetween. Fluoroscopic localizer 136 includes a processor which digitizes the image on the plate 140 and provides the digitized image to processor 104 for storage in memory 106. Processor 104 may simulate the generation of this two-dimensional x-ray image by creating a two-dimensional projection of the three-dimensional skeletal elements that have been discriminated in the image data set stored in memory 106. In order to form the displaced data set and thus achieve registration, an iterative process is used which repositions the images of the skeletal elements such that a two-dimensional projection through the displaced data set matches the actual radiographic image. The described process can utilize more than one radiographic image. Since the processor 104 is also aware of the position of the fluoroscopic localizers because of the emitters 142 thereon, which are in communication with localizer 108, the exact position of the skeletal elements during the procedure is determined.

The above solutions achieve registration by the formation of a displaced image data set stored in memory 122 which matches the displacement of the skeletal elements at the time of the procedure. An alternative technique to achieve registration is to ensure that the positions of the skeletal elements during the procedure are identical to that found at the time of imaging. This can be achieved by using a frame that adjusts and immobilizes the patient's position. In this technique, at least three markers are placed on the skin prior to imaging. These markers have to be detectable by the imaging technique employed and are called fiducials. A multiplicity of fiducials is desirable for improving accuracy.

During the procedure, the patient's body is placed on a frame that allows precise positioning. Such frames are commonly used for spinal surgery and could be modified to allow their use during imaging and could be used for repositioning the patient during the procedure. These frames could be equipped with drive mechanisms that allow the body to be moved slowly through a variety of positions. The fiducials placed at the time of imaging are replaced by emitters. By activating the drive mechanism on the frame, the exact position of the emitters can be determined during the procedure and compared to the position of the fiducials on the preprocedural image data set stored in memory 106. Once the emitters assume a geometry identical to the geometry of the fiducials of the image data set, it is considered that the skeletal elements will have resumed a geometric relationship identical to the position during the preprocedural scan, and the procedure can be performed using the unaltered image data set stored in memory 106.

In general, instrumentation employed during procedures on the skeleton is somewhat different than that used for cranial applications. Rather than being concerned with the current location, surgery on the skeleton usually consists of placing hardware through bones, taking a biopsy through the bone, or removing fragments. Therefore, the instrumentation has to be specialized for this application.

Figure 8:
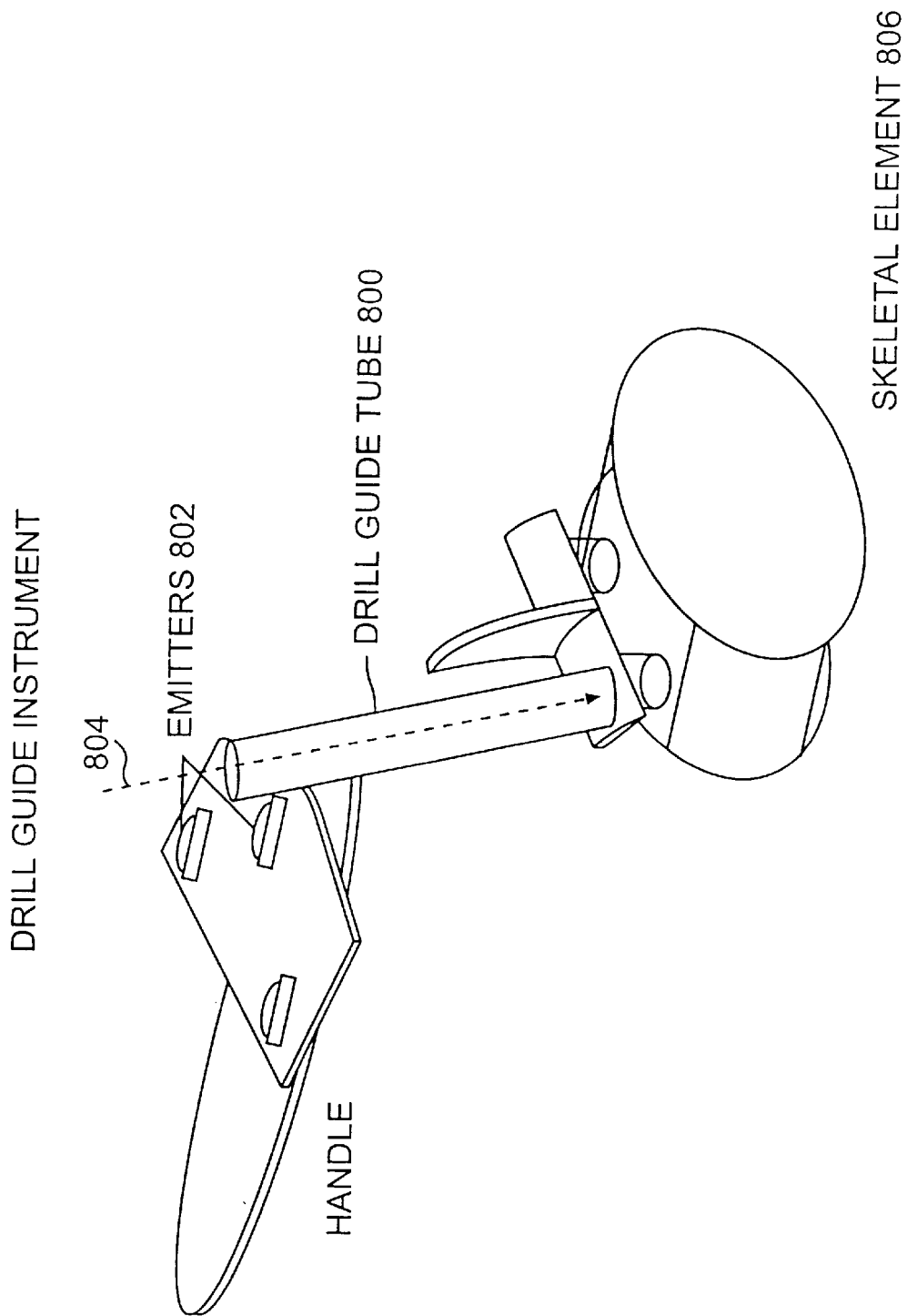
FIG. 8 is an illustration of a drill guide instrument of the invention wherein the position of a drill guide relative to the body elements may be displayed.

One instrument that is used commonly is a drill. By placing emitters on a surgical drill, and by having a fixed relationship between the drill body and its tip (usually a drill bit), the direction and position of the drill bit can be determined. At least three emitters would be needed on the drill, as most drills have a complex three-dimensional shape. Alternatively, emitters could be placed on a drill guide tube 800 having emitters 802, and the direction 804 of the screw being placed or hole being made could be determined by the digitizer and indicated on the image data set (see FIG. 8). The skeletal element 806 would also have emitters thereon to indicate its position.

Besides modification of existing instrumentation, new instrumentation is required to provide a reference system for surgery as discussed above. These reference frames, each equipped with at least 3 emitters, require fixation to the bone which prevents movement or rotation.

Figure 9:
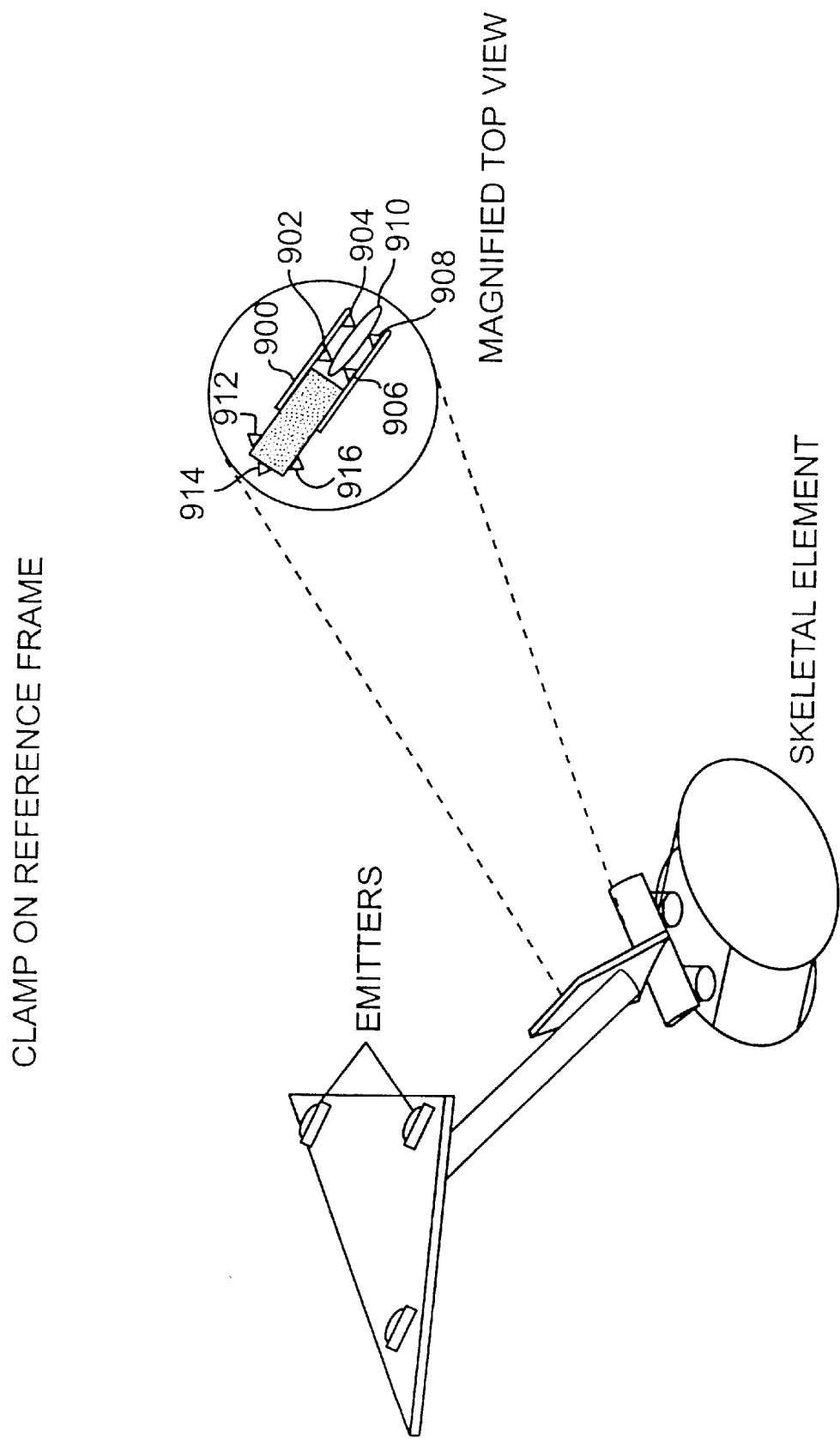
FIGS. 9 and 10 illustrate a clamped reference frame and a wired reference frame, respectively.

For open surgery, a clamp like arrangement, as depicted in FIG. 9, can be used. A clamp 900 is equipped with at least two points 902, 904, 906, 908 which provide fixation to a projection 910 of a skeletal element. By using at least two point fixation the clamp 900, which functions as a reference frame, will not rotate with respect to the skeletal element. The clamp includes emitters 912, 914, 916 which communicate with the array to indicate the position of the skeletal element as it is moved during the procedure.

Figure 10:
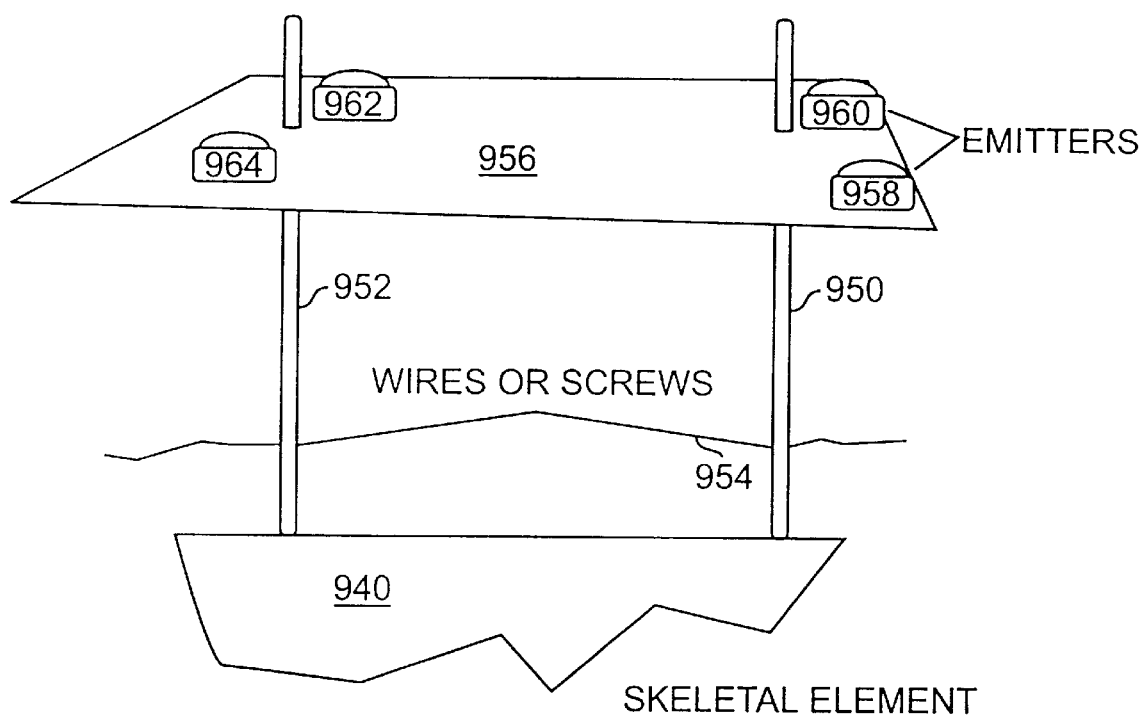

Many procedures deal with bone fragments 940 which are not exposed during surgery, but simply fixated with either wires or screws 950, 952 introduced through the skin 954. FIG. 10 depicts a reference platform 956 attached to such wires or screws 950, 952 projecting through the skin 954. The platform 956 includes a plurality of emitters 958, 960, 962, 964 which communicate with the array to indicate the position of the bone fragment 940 as it is moved during the procedure.

The reference frame can be slipped over or attached to the projecting screws or wires to establish a reference system. Alternatively, the frame can be attached to only one wire, as long as the method of attachment of the frame to the screw or wire prevents rotation, and that the wire or screw cannot rotate within the attached skeletal element.

Figure 11:
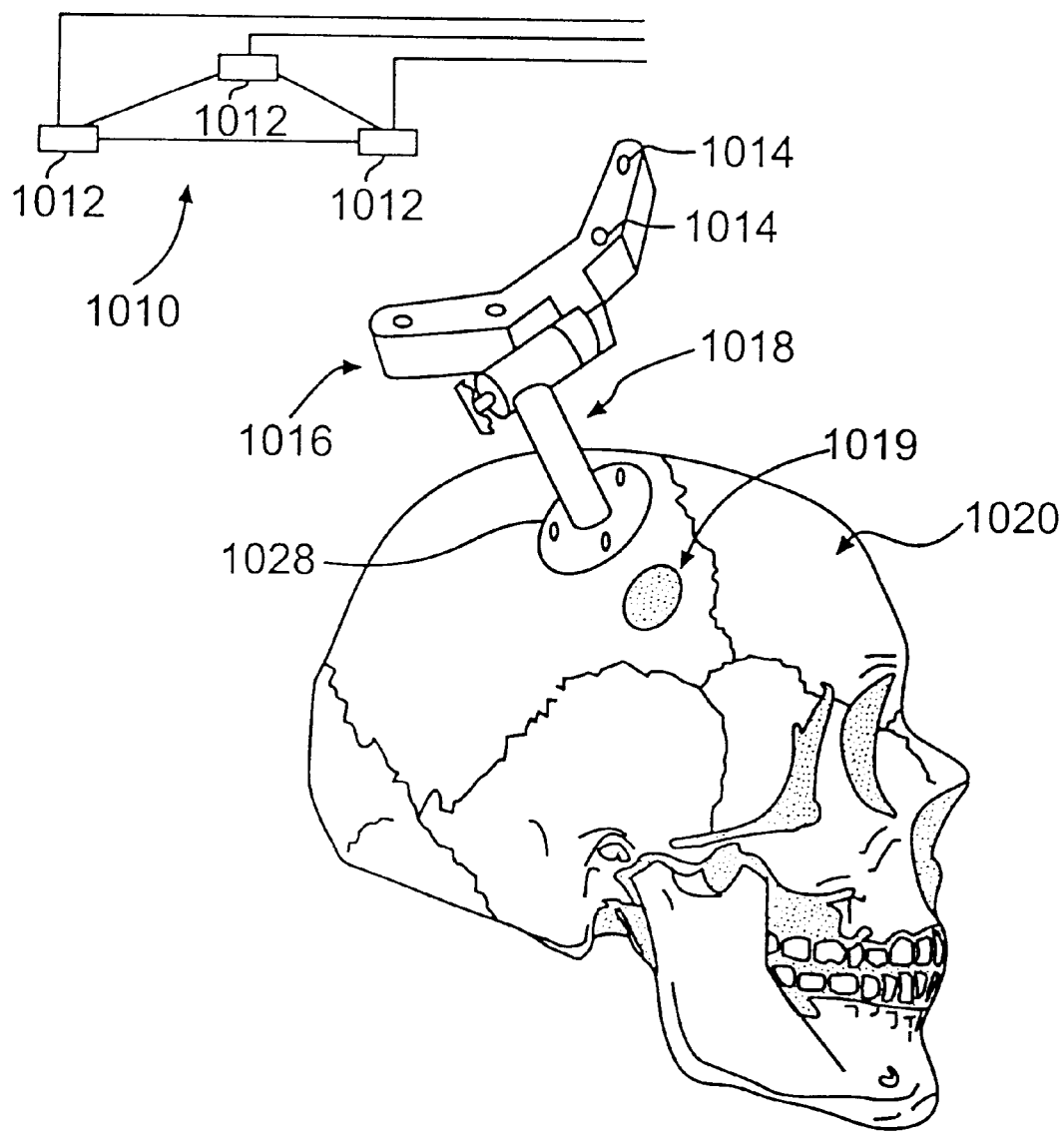
FIG. 11 is an illustration of an embodiment of a frameless stereotactic image guided cranial system.

Another embodiment of the present invention directed to cranial surgery is shown in FIG. 11. This embodiment allows for frameless stereotactic image guided cranial surgery, particularly skull surgery, without securing the patient's skull during the procedure. Rather than using implanted fiducials as reference points, anatomical landmarks, including sutural anatomy, which do not move in the skull base, are used as reference points. The use of anatomical fiducials gives better results than applied scalp fiducials. A three dimensional reconstruction of the surface of the skull allows for proper selection of these anatomic fiducials. Using the anatomical fiducials and a small FOV, the registration errors can be as low as about 0.3 mm–0.5 mm, which are less than those using implantable fiducials, and at the same time, anatomical fiducials avoid the use of implantable fiducials with their inherent problems.

The skull is imaged pre-procedurally by one of the imaging modalities (CT, MRI, etc.) as noted above for the previous embodiments. However, in this embodiment, the anatomical fiducials will be used as reference points and the images of the skull should be sufficiently detailed to show the sutural anatomy.

By way of example only, if CT were the imaging modality, a 10 cm FOV and 1 mm slice thickness would be used with the FOV centered on the temporal bone. This prescription allows the sutural anatomy, as well as other discrete surface landmarks on the skull, to be visible on the images and to be used as fiducials.

The system of FIG. 2B can also be used for this cranial embodiment. Thus, the scanner interface 102 of FIG. 2B, as discussed above, allows processor 104 to apply a discrimination process to the preprocedural image data set so only the rigid structures (the skull base and the sutural anatomy) in the skull base remain in memory 106. As also described above, the discrimination process may occur on the data which remains in memory 106 and the discriminated data would be stored in a separate memory (not shown).

Preferably, at least three reference points are then chosen by the surgeon as anatomic fiducials that are visible on the preprocedural images. The reference points may include structures that are either easily accessible to the probe or will appear to the contour scanner, ultrasound scanner, etc., during the registration process. Such structures include the mastoid tip, emissary foramen, asterion, etc. The reference points should be spaced from one another by as great a distance as possible for the greatest accuracy in the registration process. The reference points in the skull are registered in the same way as described above for the skeletal elements 10, 20, and 30, both by exposing and touching the reference points and alternatively by using a contour scanner, ultrasound scanner, etc., the detailed description of which will not be repeated here.

During the surgical procedure it may be necessary to reposition the skull, which will require the processor 104 to cause the software to reposition the image of the skull to match the new surgical position, in order to maintain registration. This repositioning of the skull is done in a substantially similar manner to that discussed above for the spine. Generally, however, the localizer 108 determines the position of the reference frame 1016, which is attached to the skull, in relation to the reference array 110 and the procedure room as previously explained. Then, as further described below, processor 104 executes the software, which maintains the registration of the image of the skull to reflect the new position of the skull base in the procedure room.

Localizer 108 is used to determine the location of the reference points and reference frame 1016 during the procedure. In general, the localizer 108 may include a digitizer, which may further include a conventional reference array 1010 that uses sensors 1012, to detect emissions from a plurality of frame emitters 1014 attached to a reference frame 1016, as shown in FIG. 11. As noted above, however, localizer 108 could also be a contour scanner, etc. Usually, the frame emitters 1014 comprise an energy transmission sources, such as sound, light, or other electromagnetic radiation sources. The frame emitters 1014 are attached to a reference frame 1016, which in turn is attached to the skull, while a reference array 1010 is placed an appropriate distance away in the procedure room. It is understood that the reverse positioning may also be used in the alternative, i.e., the reference array 1010 with sensors 1012 may be attached to the skull, with the frame emitters 1014 placed an appropriate distance away in the procedure room.

Figure 12A:
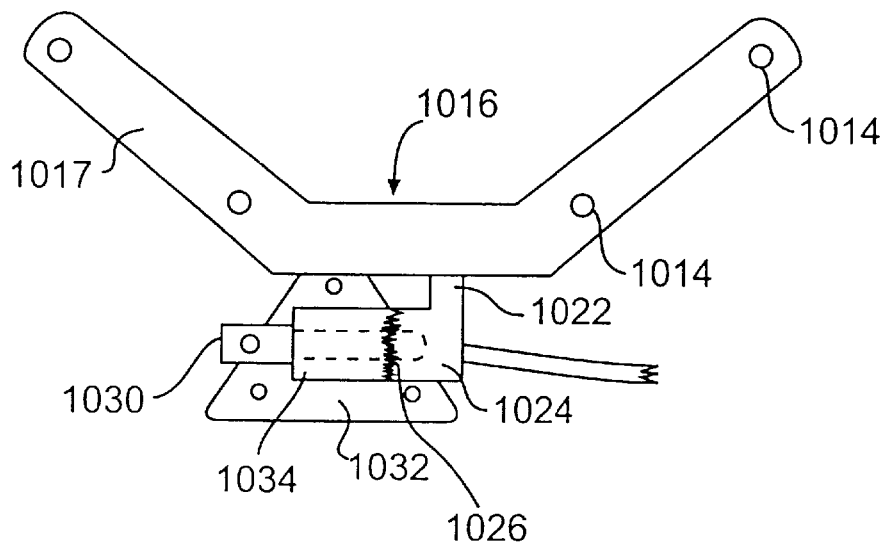
FIGS. 12A and 12B are illustrations of a part of the system of FIG. 11.

According to a preferred embodiment of the invention as shown in FIG. 11, a post 1018 having reference frame 1016 mounted thereon is attached to the skull 1020 with screws 1026 near the craniotomy 1019 at the beginning of the skull procedure. The preferred embodiment of the reference frame 1016 is shown in more detail in FIGS. 12A and 12B and is generally C-shaped, although any other planar, nonlinear shape could be used. The reference frame 1016 preferably has four frame emitters 1014 located on the top portion of the C-shaped portion 1017. It may have more or fewer frame emitters 1014, but there must be at least three noncollinear frame emitters. The reference frame 1016 also preferably has an arm 1022 and an extension 1024 with a star-burst configuration 1026 (24 teeth 0.040" deep) around a center hole 1028 for attachment to the post 1018 by a center screw 1030, described below. Such a configuration allows the reference frame 1016 to be positioned such that the emission from the frame emitters 1014 can be received as needed by the sensors 1012. However, it should be understood that other embodiments of the post 1018, arm 1022, and extension 1024 are acceptable as long as the reference frame 1016 can be fixed in relation to the skull during the procedure.

Figure 12B:
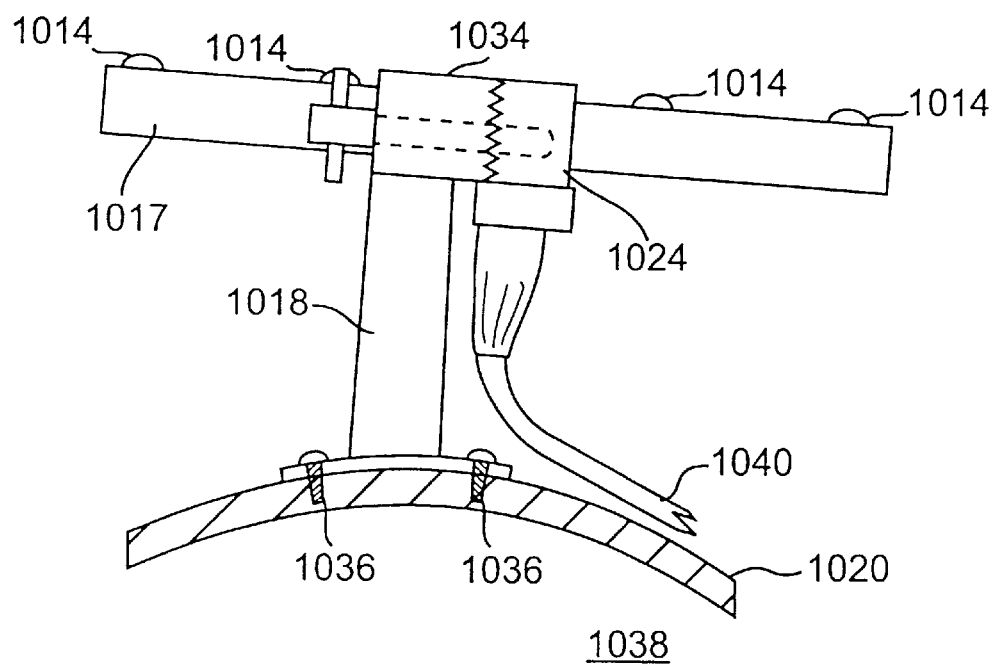

The post 1018 is preferably made of stainless steel tubing that is approximately 0.5 inches in diameter, is variable in length, but approximately 1–2 inches in length, and has a wall thickness of approximately 0.2 inches. However, other suitable, rigid materials and other sizes would also be acceptable. Some of the acceptable materials include carbon fiber, titanium, aluminum, ceramic, etc. FIG. 12B shows a top portion 1034 of an embodiment of post 1018 for attachment to reference frame 1016. The top portion 1034 is set at about a 90° angle relative to the post 1018 and has a corresponding star burst configuration and a center set screw 1030 for attachment to the reference frame 1016. The bottom portion 1032 of the post 1018 is preferably circular in shape, but may be rectangular or have any other appropriate shape, and presents a curved surface to generally correspond to the shape of the skull 1020 near the craniotomy 1019. The bottom portion 1032 and the post 1018 is attached to the skull by screws 1036, which are typical bone screws used for cranial applications and do not penetrate into the cranial space 1038.

Figure 13:
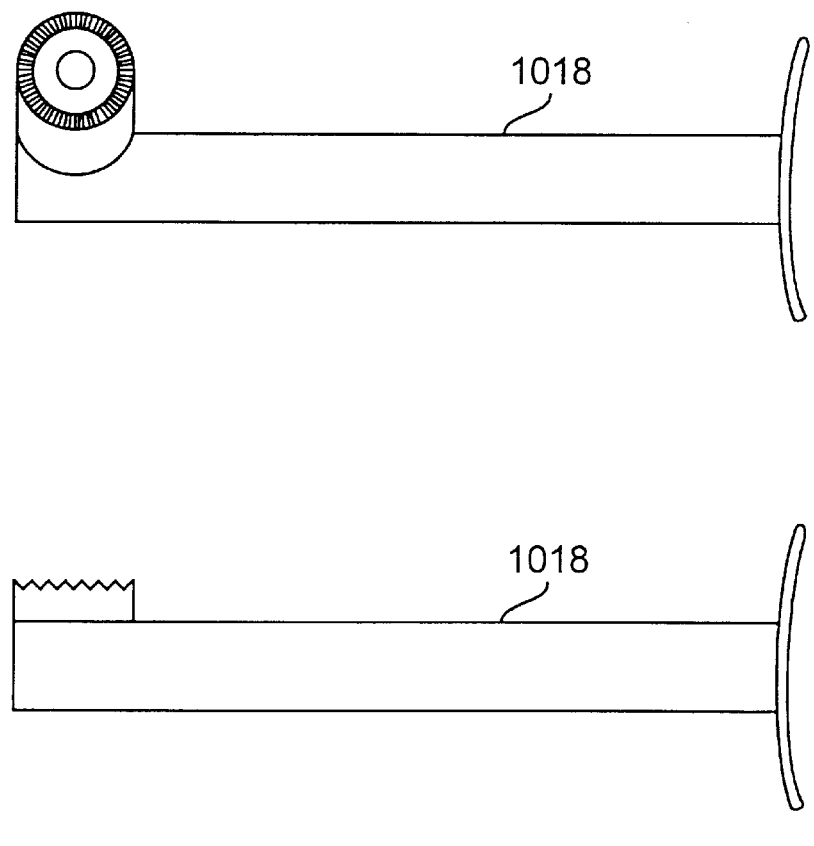
FIG. 13 is an illustration of another part of the system of FIG. 11.
Figure 14:
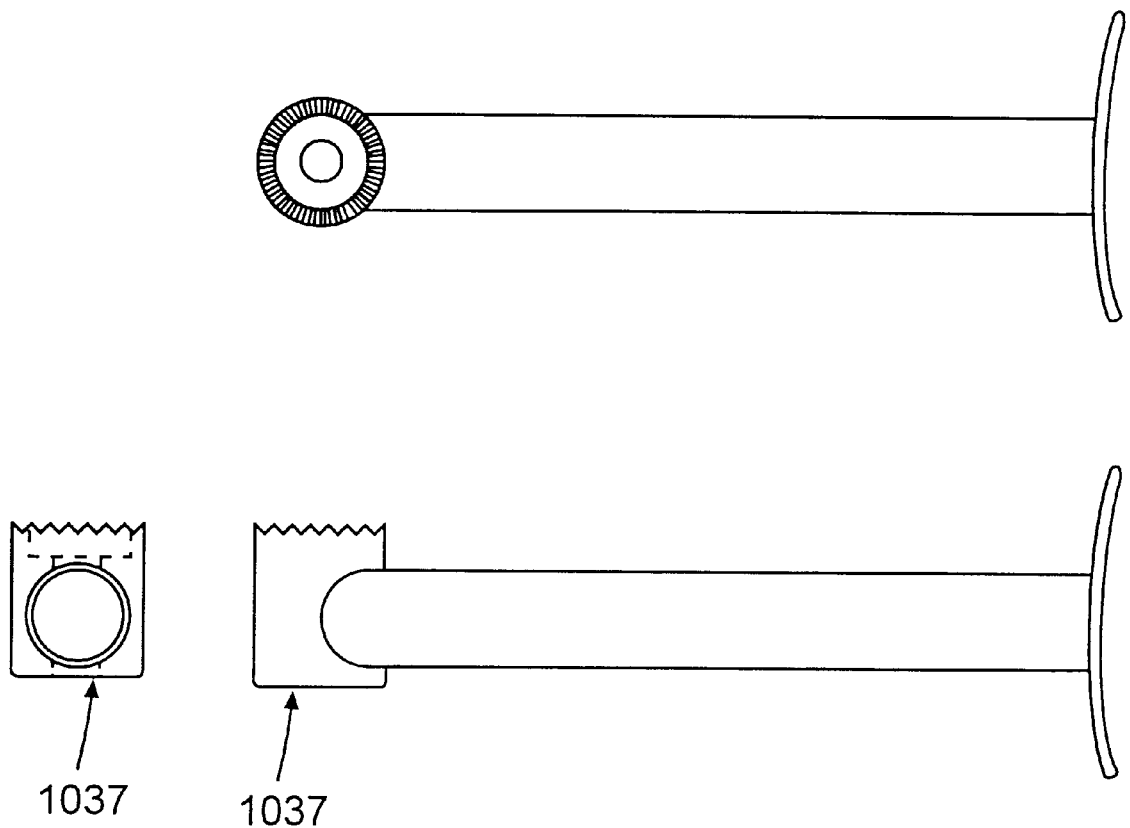
FIG. 14 is an illustration of another embodiment of a part of the system of FIG. 11.
Figure 15:
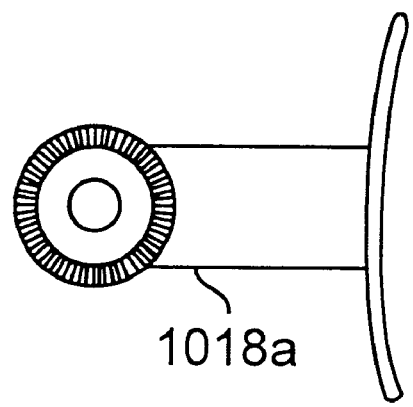
FIG. 15 is an illustration of another embodiment of a part of the system of FIG. 11.
Figure 15:
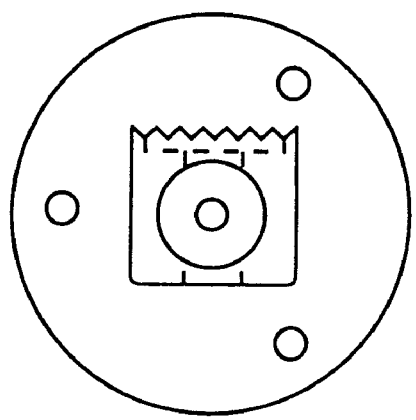
Figure 15:
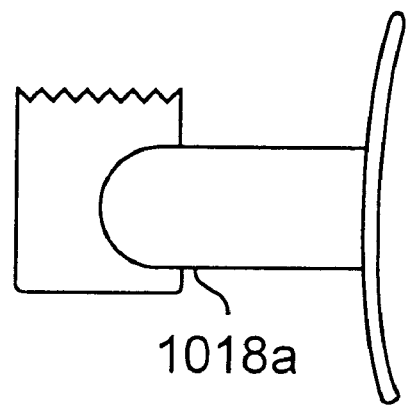

FIGS. 13, 14, and 15 show alternative embodiments of the post 1018 and the top portion 1034. The post 1018 in FIG. 13 has a top portion 1035 that is offset from the post 1018. The other elements associated with post 1018 are similar to those in FIGS. 12A and 12B. The top portion 1037 of the post in FIG. 14 is, similar to the top portion 1034 in FIGS. 12A and 12B, directly on top of the post. The post 1018a in FIG. 15 is the same as the post in FIG. 14 except that it is approximately 2 inches long rather than approximately four inches long.

Reference array 1010 is made of a suitable rigid material such as aluminum, approximately 250 to 1000 mm in length, and equipped with a plurality of sensors 1012. The reference array 1010 is positioned in the procedure room and can be remote from the reference frame 1016 and patient, so long as the energy emitted from the frame emitters 1014 can be received by the sensors 1012. The frame emitters 1014 communicate with the sensors 1012 on the reference array 1010 and, together with the processor 104 define a three-dimensional procedural coordinate system with respect to the skull 1020. The frame emitters 1014 emit a signal which is received by the sensors 1012. The received signal is digitized to compute position, for example, by triangulation. Through such information, the localizer 108, or a digitizer that is a part of the localizer 108, can determine the three-dimensional position of the frame emitters 1014 relative to the sensors 1012. Thus, localizer 108 or the processor 104 can determine the position of the reference frame 1016 relative to the array which is free to move except during localization, e.g., activation of the emitters 1014 on the reference frame 1016, as discussed above for the other embodiments. Frame emitters 1014 on the reference frame 1016 are energized and the emission of signals are controlled via cable 1040 (FIG. 12B). The signals from the frame emitters 1014 are received by the sensors 1012. The sensors 1012 in turn provide signals to the localizer 108 for determining the position of the reference frame 1016 relative to the reference array 1010.

Figure 16:
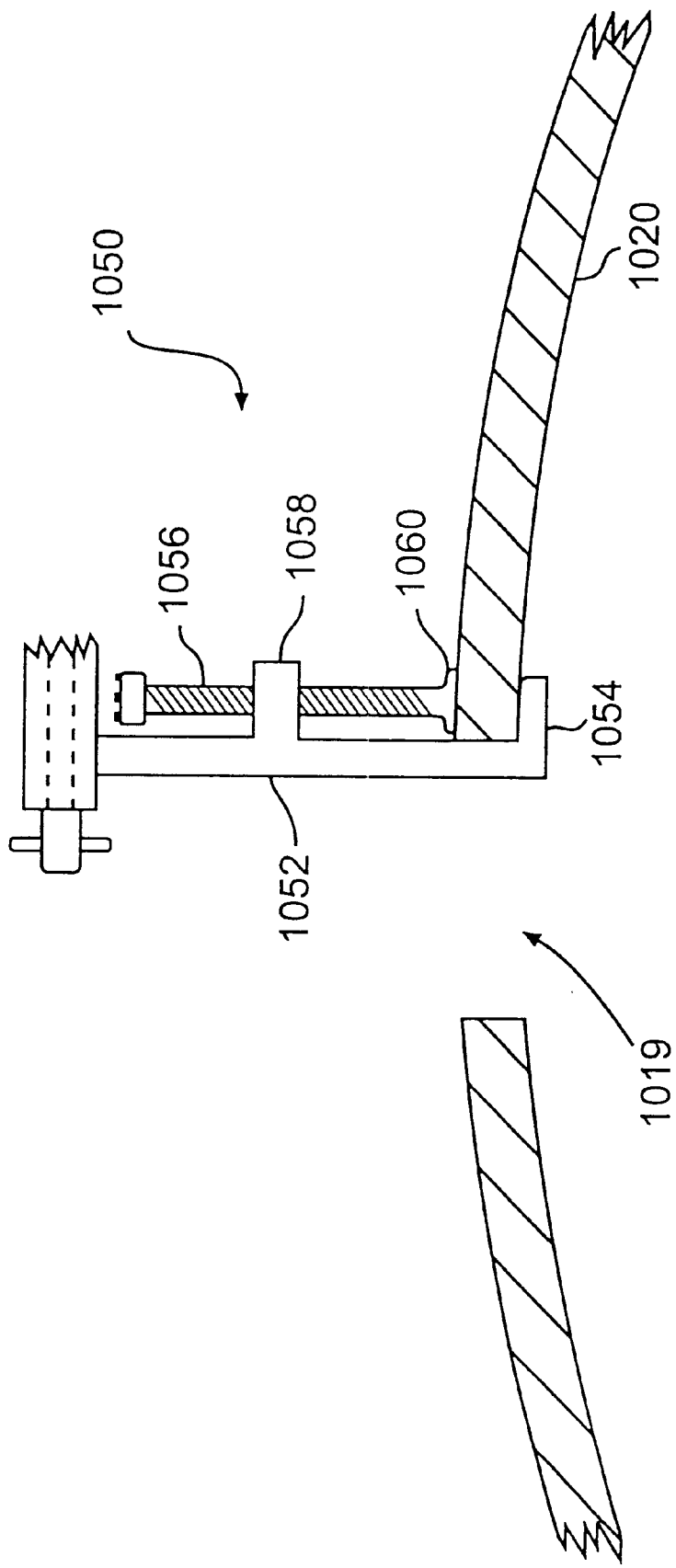
FIG. 16 is an illustration of another embodiment of a part of the system of FIG. 11.

An alternative embodiment for attaching the post 1018 to the skull 1020 is shown in FIG. 16. Rather than screwing the post into the skull, a clamp 1050 is used to secure a post having a similar top portion 1034 as shown in FIGS. 11–13 above to the skull 1020, although any appropriate configuration may be used. In this embodiment, the clamp 1050 preferably has an elongated portion 1052 which terminates in a clamp footplate 1054. A screw post 1056, which extends through an extension 1058 from the elongated member 1052 and has threads to match the screw post (not shown), has a clamping foot 1060. The post 1018 is attached to the skull at the edge of the craniotomy 1019 by screwing the clamping foot 1060 until it secures the skull 1020 against the footplate 1054. The reference frame 1016 attaches to the post 1018 in this embodiment in the same way as discussed above.

Figure 17:
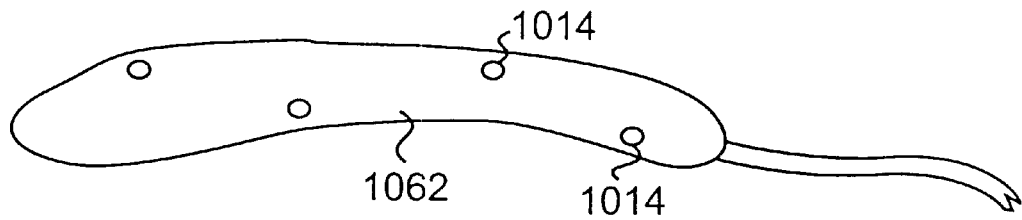
FIG. 17 is an illustration of another embodiment of a part of the system of FIG. 11.
Figure 18:
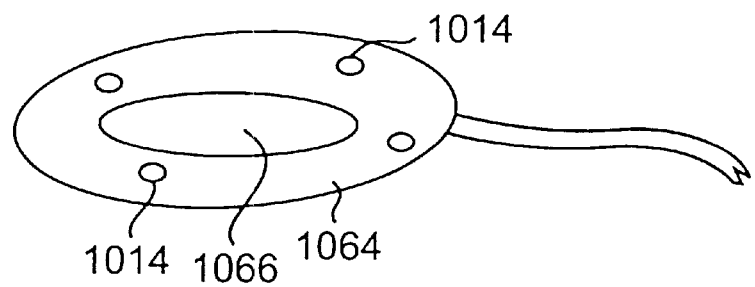
FIG. 18 is an illustration of another embodiment of a part of the system of FIG. 11.
Figure 19:
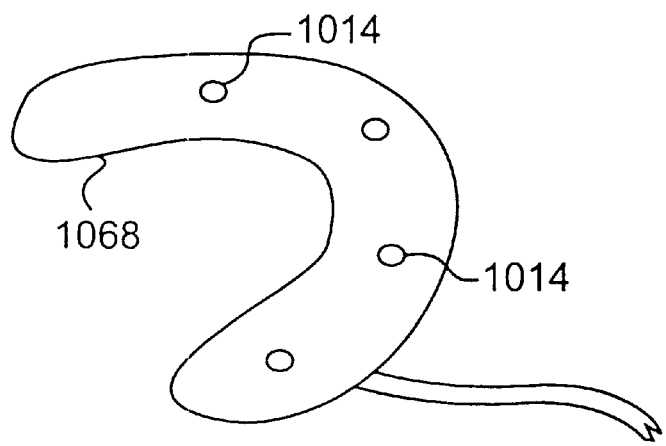
FIG. 19 is an illustration of another embodiment of a part of the system of FIG. 11.

Rather than using the reference frame 1016 mounted to the skull 1020 by either the post 1018 or the clamp 1050 shown above in FIGS. 11 and 16, respectively, the three-dimensional procedural coordinate system may alternatively be defined by emitters 1014 directly attached to the skull or the skin near the craniotomy 1019 by using self-adhesive reference pads as shown in FIGS. 17–19. The pads may be either soft self-adhesive reference pads or rigid self-adhesive reference pads. A preferred embodiment of the self-adhesive reference pad is shown in FIG. 17 and is an elongated, soft self-adhesive reference pad 1062 that is approximately three to four inches long, approximately one inch wide, and carries four frame emitters 1014. Again, there must be at least three noncollinear frame emitters on the reference pad 1062.

Soft self-adhesive reference pad 1064 is shown in FIG. 18 and is similar to reference pad 1062 shown in FIG. 17, but reference pad 1064 is circular in shape with hole 1066 in the middle for placement around the craniotomy 1019. Reference pad 1068 shown in FIG. 19 is also similar to reference pads 1062 and 1064, but is in a C-shaped pad. Pads 1062, 1064, and 1068 may also be rigid self-adhesive reference pads rather than the soft, deformable reference pads shown in FIGS. 17–19. The rigid reference pad is deformable when heated and then becomes rigid upon cooling. The location of the rigid pad is determined before the surgical procedure and the pad is heated and located in the predetermined location. The rigid pad is then allowed to cool and become rigid. The location of the rigid pad is marked and sterilized for use in the procedure since it will be in the sterile field. During the surgical procedure, the sterilized pad is attached to the predetermined location with an appropriate adhesive (not shown). It is to be understood that the reference pads may be of different sizes and shapes than those specifically illustrated here and still be within the scope of the invention.

In view of the above, it will be seen that the several objects of the invention are achieved and other advantageous results attained.

As various changes could be made in the above without departing from the scope of the invention, it is intended that all matter contained in the above description and shown in the accompanying drawings shall be interpreted as illustrative and not in a limiting sense.

We claim:

1. A system for use during a medical or surgical procedure on a head, said system generating a display representing the position of the head during the procedure based on an image data set generated prior to the procedure, the image data set having a plurality of anatomical reference points for the head, the anatomical reference points having a fixed spatial relation to the head, said system comprising:

means for identifying during the procedure the position of each of the plurality of anatomical reference points, said means for identifying including a reference frame, wherein the reference frame is attached to an opening in the skull with a C-clamp-type member;

a processor for locating portions of the image data set corresponding to the identified position of each of the plurality of reference points during the procedure, said processor generating an updated image data set representing the position of the head during the procedure; and a display for displaying an updated image utilizing the updated image data set generated by the processor.

2. A system for use during a medical or surgical procedure on a head, said system generating a display representing the position of the head during the procedure based on an image data set generated prior to the procedure, the image data set having a plurality of anatomical reference points for the head, the anatomical reference points having a fixed spatial relation to the head, said system comprising:

means for identifying during the procedure the position of each of the plurality of anatomical reference points, said means for identifying including a reference frame, wherein the reference frame is a self-adhesive pad having radiation sources thereon, and is attached directly to the skull;

a processor for locating portions of the image data set corresponding to the identified position of each of the plurality of reference points during the procedure, said processor generating an updated image data set representing the position of the head during the procedure; and a display for displaying an updated image utilizing the updated image data set generated by the processors, wherein the pad is deformable when heated and becomes substantially rigid upon cooling.

3. The system of claim 2 wherein the reference pad is circular and includes an aperture for placement on the skull.

4. The system of claim 2 wherein the reference pad is C-shaped.

5. A system for indicating a location within a body part of a patient, said system comprising:

a reference frame clamped to the body part at an entry point on the body part, said reference frame including
a post having a first end and a second end, the first end of said post being mountable directly to the body part at the entry point;
a connector portion joined to the second end of the post; and
a first plurality of radiation sources mounted to the connector portion;

an array of receivers for receiving radiation from said radiation sources and providing a reference point;

an imager to generate images of the body part, said images including a plurality of reference points, the plurality of reference points having a fixed spatial relation to the body part;

a surgical probe with a tip, the probe including a second plurality of radiation sources;

a computer operatively connected to the receiver array, the computer including a computer program for determining a position of the tip of the surgical probe relative to the receiver array using the second plurality of radiation sources and for determining the position of the first plurality of radiation sources, and a program for translating the determined position of the tip of the surgical probe to provide a translated position of the tip within a coordinate system corresponding to the images of the body part; and a display for displaying an image of the body part to provide a displayed image which corresponds to the translated position of the tip of the surgical probe.

6. The system of claim 5 further including a localizer for sensing energy emitted from the first and second plurality of radiation sources.

7. The system of claim 6 wherein the first and second plurality of radiation sources emit electromagnetic radiation.

8. The system of claim 6 wherein the first and second plurality of radiation sources emit light.

9. The system of claim 6 wherein the localizer includes a digitizer.

10. The system of claim 6 wherein the first and second plurality of radiation sources comprises at least three energy emitters.

11. The system according to claim 5 wherein the reference points are anatomical points.

12. A system for use during a medical or surgical procedure on a head, said system generating a display representing the position of the head during the procedure based on an image data set generated prior to the procedure, the image data set having a plurality of reference points for the head, the reference points having a fixed spatial relation to the head, said system comprising:

means for identifying during the procedure the position of each of the plurality of reference points, said means for identifying including a reference frame connected with a C-clamp-type member to an opening in the head at a first end; and a planar portion connected to a second end of the reference frame;

a processor for locating portions of the image data set corresponding to the identified position of each of the plurality of reference points during the procedure, said processor generating an updated image data set representing the position of the head during the procedure; and a display for displaying an updated image utilizing the updated image data set generated by the processor.

13. A system for use during a medical or surgical procedure on a head, said system generating a display representing the position of the head during the procedure based on an image data set generated prior to the procedure, the image data set having a plurality of reference points for the head, the reference points having a fixed spatial relation to the head, the system including means for identifying during the procedure the position of each of the plurality of reference points, said means for identifying including a reference frame; a processor for locating portions of the image data set corresponding to the identified position of each of the plurality of reference points during the procedure, said processor generating an updated image data set representing the position of the head during the procedure; and a display for displaying an updated image utilizing the updated image data set generated by the processor, said reference frame including:

a reference frame clamped to the head at an entry point on the head, said reference frame including a post having a first end and a second end, the first end of said post being connected to the head at the entry point; and a planar portion connected to the second end of the post.

14. The system according to claim 13 wherein the reference points are anatomical points.

15. A system for use during a medical or surgical procedure on a head, said system generating a display representing the position of the head during the procedure based on an image data set generated prior to the procedure, the image data set having a plurality of reference points for the head, the reference points having a fixed spatial relation to the head, said system comprising:

means for identifying, during the procedure, the position of each of the plurality of reference points, said means for identifying including a reference frame clamped to the head at an entry point on the head, said reference frame including a post having a first end and a second end, the first end of said post being connected to the head at the entry point; and a planar portion connected to the second end of the post;

a processor for locating portions of the image data set corresponding to the identified position of each of the plurality of reference points during the procedure, said processor generating an updated image data set representing the position of the head during the procedure; and a display for displaying an updated image utilizing the updated image data set generated by the processor.

16. The system of claim 15 wherein the identifying means further includes a probe, the probe having a plurality of radiation sources.

17. A system for use during a medical or surgical procedure on a head, said system generating a display representing the position of the head during the procedure based on an image data set generated prior to the procedure, the image data set having a plurality of reference points for the head, the reference points having a fixed spatial relation to the head, the system including means for identifying during the procedure the position of each of the plurality of reference points, said means for identifying including a reference frame; a processor for locating portions of the image data set corresponding to the identified position of each of the plurality of reference points during the procedure, said processor generating an updated image data set representing the position of the head during the procedure; and a display for displaying an updated image utilizing the updated image data set generated by the processor, said reference frame including:

a C-clamp-type member connecting a first end of the reference frame to an opening in the head; and a planar portion at a second end of the reference frame, the planar portion having radiation sources.

18. A system for use during a medical or surgical procedure on a head, said system generating a display representing the position of the head during the procedure based on an image data set generated prior to the procedure, the image data set having a plurality of reference points for the head, the reference points having a fixed spatial relation to the head, the system including means for identifying during the procedure the position of each of the plurality of reference points, said means for identifying including a reference frame; a processor for locating portions of the image data set corresponding to the identified position of each of the plurality of reference points during the procedure, said processor generating an updated image data set representing the position of the head during the procedure; and a display for displaying an updated image utilizing the updated image data set generated by the processor, said reference frame including:

a self adhesive pad attached directly to the head, the self adhesive pad having radiation sources thereon, wherein the pad is deformable when heated and becomes substantially rigid upon cooling.

19. The system of claim 18 wherein the reference pad is circular and includes an aperture for placement on the skull.

20. The system of claim 18 wherein the reference pad is C-shaped.

* * * * *

UNITED STATES PATENT AND TRADEMARK OFFICE
CERTIFICATE OF CORRECTION

PATENT NO.     : 6,167,145
DATED          : December 26, 2000
INVENTOR(S)    : Kevin T. Foley et al.

It is certified that error appears in the above-identified patent and that said Letters Patent is hereby corrected as shown below:

Title page, column 1,
Item [75], line 3, "Germantown, Tenn." should read -- Superior, Colo. --.

Claim 2, column 15,
Line 39, "the procesors" should read -- the processor --.

Signed and Sealed this

Second Day of October, 2001

*Attest:*

NICHOLAS P. GODICI
*Attesting Officer*   Acting Director of the United States Patent and Trademark Office